(12) United States Patent
Paoles et al.

(10) Patent No.: US 11,406,828 B2
(45) Date of Patent: Aug. 9, 2022

(54) METHOD AND SYSTEM FOR PROVIDING MULTI-CHANNEL AND/OR VARIABLE NEUROSTIMULATION

(71) Applicant: ONWARD MEDICAL N.V., Eindhoven (NL)

(72) Inventors: Edoardo Paoles, Eindhoven (NL); Mathieu Scheltienne, Eindhoven (NL); Jeroen Tol, Eindhoven (NL)

(73) Assignee: ONWARD MEDICAL N.V., Eindhoven (NL)

( * ) Notice: Subject to any disclaimer, the term of this patent is extended or adjusted under 35 U.S.C. 154(b) by 0 days.

(21) Appl. No.: 15/931,467

(22) Filed: May 13, 2020

(65) Prior Publication Data
US 2020/0360697 A1 Nov. 19, 2020

(30) Foreign Application Priority Data
May 13, 2019 (EP) .................... 19174015

(51) Int. Cl.
*A61N 1/36* (2006.01)
*A61N 1/04* (2006.01)

(52) U.S. Cl.
CPC ..... *A61N 1/36171* (2013.01); *A61N 1/36067* (2013.01); *A61N 1/36071* (2013.01); *A61N 1/36175* (2013.01); *A61N 1/36196* (2013.01)

(58) Field of Classification Search
CPC .............. A61N 1/0456; A61N 1/36025; A61N 1/3605; A61N 1/36062; A61N 1/36103; A61N 1/36171; A61N 1/36175; A61N 1/37196; A61N 1/36146
See application file for complete search history.

(56) References Cited

U.S. PATENT DOCUMENTS

| | | | |
|---|---|---|---|
| 4,398,537 A | 8/1983 | Holmbo | |
| 8,543,200 B2 | 9/2013 | Lane et al. | |
| 8,768,481 B2 | 7/2014 | Lane | |
| 2003/0200323 A1 | 10/2003 | Dold et al. | |
| 2006/0149337 A1 | 7/2006 | John | |

(Continued)

FOREIGN PATENT DOCUMENTS

| | | |
|---|---|---|
| WO | 2014005075 A1 | 1/2014 |
| WO | 2014149895 A1 | 9/2014 |

OTHER PUBLICATIONS

Courtine, G. et al., "Transformation of nonfunctional spinal circuits into functional states after the loss of brain input," Nature Neuroscience, vol. 12, No. 10, Oct. 2009, Available Online Sep. 20, 2009, 20 pages.

(Continued)

*Primary Examiner* — Carl H Layno
*Assistant Examiner* — Anh-Khoa N Dinh
(74) *Attorney, Agent, or Firm* — Finnegan, Henderson, Farabow, Garrett & Dunner, LLP

(57) ABSTRACT

Methods and systems are provided for multi-channel and/or variable neurostimulation. In one example, overlapping of stimulation events between a plurality of pulse train provided by the neurostimulation system is determined, and one or more parameters of one or more of the plurality of pulse trains are adjusted so as to reduce or avoid overlapping of stimulation events of the plurality of pulse train. The one or more parameters may include a start time, a frequency, and a pulse shape.

19 Claims, 13 Drawing Sheets

(56) References Cited

U.S. PATENT DOCUMENTS

| | | |
|---|---|---|
| 2007/0142874 A1 | 6/2007 | John |
| 2011/0054567 A1 | 3/2011 | Lane et al. |
| 2011/0054568 A1* | 3/2011 | Lane .................. A61N 1/36082 |
| | | 607/59 |
| 2011/0054570 A1 | 3/2011 | Lane |
| 2011/0160810 A1 | 6/2011 | Griffith |
| 2012/0116476 A1 | 5/2012 | Kothandaraman |
| 2014/0005753 A1* | 1/2014 | Carbunaru ......... A61N 1/36171 |
| | | 607/62 |
| 2014/0074190 A1 | 3/2014 | Griffith |
| 2014/0243923 A1 | 8/2014 | Doan et al. |
| 2015/0328462 A1 | 11/2015 | Griffith |
| 2017/0266455 A1 | 9/2017 | Steinke |

OTHER PUBLICATIONS

Dominici, N. et al., "Versatile robotic interface to evaluate, enable and train locomotion and balance after neuromotor disorders," Nature Medicine, vol. 18, No. 7, Jul. 2012, Published Online May 31, 2012, 8 pages.

Capogrosso, M. et al., "A Computational Model for Epidural Electrical Stimulation of Spinal Sensorimotor Circuits," The Journal of Neuroscience, vol. 33, No. 49, Dec. 4, 2013, 15 pages.

Wenger, N. et al., "Closed-loop neuromodulation of spinal sensorimotor circuits controls refined locomotion after complete spinal cord injury," Science Translational Medicine, vol. 6, No. 255, Sep. 24, 2014, 12 pages.

Wenger, N. et al., "Spatiotemporal neuromodulation therapies engaging muscle synergies improve motor control after spinal cord injury," Natural Medicine, vol. 22, No. 2, Feb. 2016, Available Online Jan. 18, 2016, 33 pages.

Pudo, Dominik, "Estimating Intensity Fluctuations in High Repetition Rate Pulse Trains Generated Using the Temporal Talbot Effect", IEEE Photonics Technology Letters, vol. 18, No. 5, Mar. 1, 2006 (3 pages).

Extended European Search Report for European Application No. 19174015.8-1124, dated Nov. 11, 2019 (8 pages).

* cited by examiner

METHOD AND SYSTEM FOR PROVIDING MULTI-CHANNEL AND/OR VARIABLE NEUROSTIMULATION

CROSS-REFERENCE TO RELATED APPLICATIONS

The present application claims priority to European Patent Application No. 19174015.8 filed on May 13, 2019. The entire contents of the above-listed application is hereby incorporated by reference for all purposes.

TECHNICAL FIELD

The present disclosure relates to a method and system for providing multi-channel variable neuromodulation.

BACKGROUND AND SUMMARY

Epidural electrostimulation (EES) shows promising results for spinal cord injury therapy. The mechanisms are still unclear and under investigation, but EES can both stimulate the leg muscles through the proprioceptive afferent fibers and restore the neuronal network in the spinal cord. EES uses a multi-electrode array placed on the dorsal side of the spinal cord on top of the dura matter. In rats, the combination of serotonergic agonists and EES was able to acutely transform spinal networks from non-functional to highly functional and adaptive states as early as 1 week after injury (Courtine G, et al., *Transformation of nonfunctional spinal circuits into functional states after the loss of brain input. Nature neuroscience* 12, 1333-1342, (2009)). Moreover, EES also restores voluntary control of locomotion by rewiring the injured spinal cord area (Wenger N et al., *Spatiotemporal neuromodulation therapies engaging muscle synergies improve motor control after spinal cord injury, Nature Medicine* 22, 138-145 (2016)). However, EES alone is not sufficient. Combination with either drugs injection or robotic assisted therapy such as a bodyweight support system improves the recovery (Dominici N et al., *Versatile robotic interface to evaluate, enable and train locomotion and balance after neuromotor disorders, Nature medicine* 18, 1142-1147 (2012)).

Because of the complexity of the spinal cord, delivering EES stimulation on the multi-electrode array (lead) implanted is quite challenging. Computational models were designed and tested on both rats and human (Capogrosso M, et al., *A Computational Model for Epidural Electrical Stimulation of Spinal Sensorimotor Circuits, Journal of Neuroscience* 4 Dec. 2013, 33 (49) 19326-19340) to evaluate the neuronal and muscular response to the stimulation, as well as closed-loop neuromodulation systems that refined locomotion after complete spinal cord injury (Wenger N et al., *Closed-loop neuromodulation of spinal sensorimotor circuits controls refined locomotion after complete spinal cord injury, in Science Translational Medicine, vol.* 6, num. 255, 2014).

The degree of control required on the neurostimulation restricts largely the available stimulation settings (stimulus space). The stimulation settings must comply with hardware limitations, with requirements on the predictive capability of the system and with safety regulatory norms. For instance, the hardware has a limited power supply, the stimulation outcome (muscle activation) must be controlled, and the electrode chemical stability must be insured independently of the stimulation settings used.

Moreover, each muscle has a different response according to the nerve fibers stimulation settings. Each muscle is associated with nerve fibers and a stimulation area on the implanted lead. This association is called a functional muscle block (FMB), also referred to as stimulation block (SB) in this text. The muscle response will vary with the amplitude, but also with the frequency, the pulse shape, or the use of burst of pulses rather than continuous frequency stimulation. Thus, during a gait cycle, the different FMBs need to be stimulated simultaneously with different pulsed electrical waveforms at different frequencies and amplitudes, sometimes with different pattern of pulses, in order to reproduce a normal-like cycle. Multiple channels (i.e. multiple FMBs, pulsed electrical waveforms) variable frequency neurostimulation is harder to control since the neurostimulation's pulses might temporally overlap in time. Overlapping of pulses creates several issues:

It is hardly possible to output 2 pulses on the same electrode simultaneously

If the electrodes are different, the overlapping of 2 pulses will require a higher voltage on the power supply line, and thus will draw out more power from the battery than if they were outputted one after the other. This second point is critical in implantable devices since the battery life time is one of the main concerns.

The muscle response (outcome) achieved with temporally overlapping pulses will potentially differ from the outcome reached with the same pulses taken separately. Current knowledge of the muscle response induce by spinal cord neurostimulation is limited to strictly orthogonal pulsing.

Thus, to stimulate in a controlled fashion and in a secure way, while drawing as little power as possible from the battery, a solution to avoid temporal overlap of the pulses is needed.

One method to avoid overlap of the pulses between pulsed electrical waveforms is to allow only one pulse at a time, and to delay the others. The method, called the "token approach", is described in the patent "US20110054568A1" assigned to the "Boston Scientific Neuromodulation Corporation". If 2 pulse generators want to output a pulse at the same time, one gets the priority and the other is delayed. Other patents on close-by methods identified as pulse positioning methods were also filed by the same company ("U.S. Pat. No. 8,543,200B2", "U.S. Pat. No. 8,768,481B2"). They aim to place the pulses on the timeline in such a way that pulses don't bump into each other, in other words, that overlap is avoided. With these methods, each pulsed electrical waveform will not have a constant frequency, but an instantaneous frequency within a jitter specification. For instance, the requirement can bound the jitter at 10% of the nominal frequency for each pulsed electrical waveform. Thus, at any given instant, a pulsed electrical waveform at the nominal frequency 40 Hz will have its instantaneous frequency between 36 Hz and 44 Hz.

US 2003/1200323 A1 relates to a re-chargeable spinal cord stimulator system, which includes multiple electrodes, multiple, independently programmable, stimulation channel with an implantable pulse generator, which channels can provide concurrent, but unique stimulation fields, permitting virtual electrodes to be realized.

U.S. Pat. No. 4,398,537 relates to an independently rate-adjusting multiple channel controller for nerve stimulator transmitter to be used in conjunction with implanted stimulation pulse output unit, wherein an event that two or more trigger signals coincide in the transmitting circuit, the rate control circuit blocks and delays the latter occurring trigger signal with only minor or insignificant effect on a trigger signal rate.

WO 2014/005075 A1 and US 2014/0005753 A1 relates to a system compounding low-frequency sources for high-frequency neuromodulation, where the system has a control circuitry configured for operating the switching network to concurrently convey the plurality of electrical pulse trains for a plurality of electrical terminals to a common electrical terminal, thereby creating a combined electrical pulse train having an average pulse rate equal to or greater than 1 KHz.

US 2011/0160810 A1 relates to a multi-channel neurostimulation system comprising a plurality of electrical terminals configured for being respectively coupled to a plurality of electrodes, stimulation output circuitry including electrical source circuitry of the same polarity configured for generating a polarity of pulse electrical waveforms in a plurality of timing channels. Furthermore, there is a control circuitry configured for instructing the stimulation output circuitry to serially couple the electrical source circuitry to different sets of the electrodes when pulses of the respective pulsed electrical waveforms do not temporarily overlap each other, and for instructing the stimulation output circuitry to couple the electrical source circuitry to a union of the different electrode sets when pulses of the respective pulsed electrical waveforms temporarily overlap each other.

US 2012/0116476 A1 relates to a system and method for storing application specific and lead configuration information in a neurostimulation device, whereas the control device is able to re-program the neurostimulator.

US 2015/0328462 relates to a system and method for independently operating multiple neurostimulation channels. The system comprises a control circuitry configured for instructing the stimulation output circuitry to serially couple the electrical source circuitry to different sets of electrodes when pulses of the respective pulse electrical waveforms do not temporarily overlap each other and for instructing the stimulation output circuitry to couple the electrical source circuitry to a union of the different electrode sets when pulses of the respective pulsed electrical way forms temporarily overlap each other.

WO 2014/149895 A1 relates to a neuromodulation system method thereto. Here, a first electrical modulation energy to a patient is delivered through a timing channel at the relatively high energy level during a first time period in accordance with a stored modulation energy delivery schedule, and a second electrical modulation energy is delivered to the patient through the same timing channel at the relatively low energy level during a second level time period in accordance with the stored modulation energy delivery schedule.

Furthermore, US 2014/0074190 relates to a multi-channel neurostimulation system comprising a plurality of electrical terminals configured for being respectively coupled to a plurality of electrodes. Moreover, there is a stimulation output circuitry including electrical source circuitry of the same polarity configured for generating a plurality of pulsed electrical waveforms in a plurality of timing channels, and control circuitry configured for instructing the stimulation output circuitry to serially couple the electrical source circuitry to different sets of the electrodes when pulses of the respective pulsed electrical waveforms do not temporally overlap each other, and for instructing the stimulation output circuitry to couple the electrical source circuitry to a union of the different electrode sets when pulses of the respective pulsed electrical waveforms temporally overlap each other.

U.S. Pat. No. 8,543,200 B2 relates to methods to avoid frequency locking and a multi-channel neurostimulation system using pulse placement. A plurality of pulse electrical waveforms are respectively delivered within a plurality of timing channels of the neurostimulation system, thereby treating the patient. Sets of stimulation pulses within the electrical waveforms that will potentially overlap temporarily are predicted. Each of the potentially overlapping pulse sets is substituted with a replacement stimulation pulse, such that each replacement stimulation pulse is delivered within at least one of the respective timing channels, thereby preventing temporal overlap between the stimulation pulses of the respective electrical waveforms while preventing frequency locking between the timing channels.

US 2011/0054570 relates to a method and external control device for preventing frequency locking in a multi-channel neurostimulation system and external control device. A plurality of pulse electrical waveforms is provided. Each of the pulse electrical waveforms has a period and a pulse width. The greatest common divisor of the periods of the pulse electrical waveform is computed, and the sum of the pulse widths of the pulse electrical waveforms is computed. A plurality of timing channels and the neurostimulation is allowed to be programmed with the pulsed electrical waveforms if the greatest common divisor is equal to or greater than the sum.

It is therefore an object of the present invention to provide a solution for a system and method that can better manage partial and full overlap of multichannel and/or variable neuromodulation/neurostimulation, also using a plurality of waveforms, and to enhance multi-channel and/or variable neurostimulation.

This object is solved by the method according to claim 1. Accordingly, a method for providing multi-channel and/or variable neurostimulation is comprising at least the following steps:

Defining a finite period of time;

Providing at least a first pulse train, the first pulse train being provided on a first channel comprising a first temporal arrangement of stimulation events;

Providing at least a second pulse train, the second pulse train being provided on a second channel comprising a second temporal arrangement of stimulation events;

Analyzing the first pulse train and the second pulse train for at least one potential overlap of stimulation events and/or using an analysis whether there is at least one potential overlap of stimulation events of the first pulse train and the second pulse train;

In case of a detected overlap, adjusting the first pulse train and/or the second pulse train by:

a. Shifting the first pulse train and the second pulse train relatively to each other; and/or b. Adapting the first temporal arrangement and/or the second temporal arrangement of stimulation events within a predetermined tolerance band; and/or c. Modify at least partially the shape and/or phase duration of the stimulation events of the first pulse train and/or the second pulse train and/or the shape and/or phase duration of at least one phase of a stimulation event being part of the stimulation events of the first pulse train and/or the second pulse train; so as to avoid at least partially the overlap of stimulation events.

The invention is based on the basic idea that stimulation events happening in one or more pulse trains and an overlapping of stimulation events, which can happen in multi-channel and/or variable frequency neurostimulation, has to be avoided or minimized to limit the potential, adverse impact on the intended therapy. The overlap is dealt with by the combination of the delays with an alternative temporal arrangement and/or with an alternative shape/phase duration of the stimulation events of the pulse train for each finite stimulation period. An overlapping of pulse trains, which can have a potential impact on the intended therapy, is avoided in the multi-channel neurostimulation with variable frequencies or variable temporal arrangements.

Pulse trains forming different timing channels can no longer overlap fully or can only overlap partially and so stimulation effects that cause so called adverse side effects are prevented. Ordinary multi-channel and/or variable neurostimulation may lead to overlapping of pulse trains, which is unwanted as such overlapping may lead to unwanted effects. Such effects may happen in various ranges and may be tolerable to some extent, but for example when exceeding e.g. pre-determined criteria or pre-set boundaries, they may be intolerable and must be avoided. One important point is the finding of the inventors that defining a finite period of time, which is the relevant time frame for applying multi-channel and/or variable neurostimulation (e.g. a segment in a gait cycle), will significantly reduce the complexity for handling unwanted overlapping of neurostimulation events, pulses or pulse trains or the like. By only looking at a finite period of time, collisions or overlap events must only be recognized and be found in this finite time period and there is no need to find and avoid such events outside of such period. Thus, a better control of the neurostimulation can be provided.

The term pulse train as used in connection with the present disclosure is inter alia to be understood as a (neurostimulation) channel with one or more stimulation events such as at least one stimulation pulse occurring within the (chosen) finite period of time. Alternative terms which are to be understood as being the same or covered by the term pulse train are pulse waveform and pulsed electrical waveform.

More specifically, a pulse train in the sense of this disclosure can be understood as a finite time period with one or more stimulation events comprising at least one stimulation pulse or stimulation burst. These events are occurring within the (chosen) finite period of time. A pulse train in this sense may have its own temporal arrangement such as a periodic arrangement characterized by a frequency or any aperiodic arrangement and may be provided on a (neurostimulation) channel. There can be two pulse trains or as shown in some examples, three or even more pulse trains.

For a plurality of timing channels delivering a plurality of multiphasic pulsed electrical waveforms with equally or different temporal arrangements (e.g. frequencies), some of the pulses within the electrical waveforms may partially or fully overlap temporally with others.

The term temporal arrangement as used in connection with the present disclosure is inter alia to be understood as covering any temporal arrangement of stimulation events such as periodic or aperiodic events. It also covers one or more frequencies of stimulation events or the like, but it is not limited to such events.

The term analyzing the first pulse train and the second pulse train for at least one potential overlap of stimulation events as used in connection with the present disclosure is inter alia to be understood as covering any analysis performed online, partially online or even remotely, without delay or slight delay, or with significant delay and time shift, in real-time or not in real-time, but not limited to the foregoing options.

The term using an analysis whether there is at least one potential overlap of stimulation events of the first pulse train and the second pulse train as used in connection with the present disclosure is inter alia to be understood as covering the usage of the analyzed results which can be through storing the results in e.g. a lookup table/memory and use these parameters to generate e.g. stimulation events such as waveforms.

The term variable neurostimulation describes inter alia (but not limited only to this) that the provided neurostimulation can be varied especially in terms e.g. of frequency and/or amplitude and/or pulse width and/or pulse shape during analysis in order to find the best fitting stimulation setup.

The term neurostimulation covers any type of neurostimulation, such as spinal cord neurostimulation, invasive and/or non-invasive stimulation (also covering combinations thereof), transcutaneous neurostimulation (tSCS), stimulation to enhance or restore autonomous functions of a patient, restoration and/or enhancement of movements of any body parts such as locomotion or movement of arms and hands of a patient, restoration and/or enhancement of blood pressure control, voluntary or any other control over muscles, pain treatment, deep brain stimulation, brain stimulation, any stimulation for the organs like heart stimulation, epidural stimulation (EES), functional electrical stimulation (FES), subdural stimulation, and the like. Generally speaking the first channel and the second channel (and also any further channel) can be realized in the same channel.

Shifting of the first pulse train and the second pulse train relatively to each other can be achieved by time shifting them, i.e. creating a relative shift of the two (or more) pulse trains relatively to each other. Shifting can be done by shifting one pulse train relatively to another pulse train (e.g. 5 ms or any other suitable value between the start of the first pulse train and of the second pulse train). Also, a shifting relatively to a fixed point in time is possible (e.g. a first pulse trains starts at t=1 millisecond (ms), a second pulse train starts at t=5 ms and a third pulse train starts at t=20 ms (suitable other values are also possible)).

To avoid temporal interference of the pulses and to ensure that the intended neurostimulation result is achieved, an overlap of stimulation events shall no longer be possible or only to such an extent, which is still acceptable when considering the neurostimulation result.

The overlapping of pulses might affect the outcome of the neurostimulation. The neurostimulations outcome achieved with overlapping pulses will potentially differ from the outcome reached with the same pulses applied separately. This space-time programming procedure designed to determine the electrode configuration of each functional muscle block uses electromyography (EMG) measurements and assumes completely orthogonal pulsing while this is actually not necessary the case in the stimulation program inputted by the physiotherapist if variable frequency stimulation, variable neuromodulation, or variable neurostimulation is used.

A first step in the method is the setting of a finite period of time, as for neurostimulation usually it is possible to provide a "finite" stimulation partiture, that is, a (pre-defined "partiture" of stimulation events and/or a series of stimulation events for a certain period of time, that can be repeated. Thus, it is not necessary, to have an endless stimulation partiture but rather a repetition of stimulation events for a certain period. By this, a well-defined period of time can be identified for each segment in the "partiture" of stimulation events in which collision events can be checked. In one example, for neurostimulation, a sequence of stimulation events for a desired period of time may be provided, and the sequence of stimulations may be repeated. Further, a finite period of time may be identified, and the finite period may be applicable for each repeated sequence of stimulation events, during which overlap of stimulation events may be analyzed.

The method implemented to avoid overlap of stimulation events between at least two pulse trains adds further a delay between each of the pulse trains, which is called a shift and may replace the desired frequency set of these pulse trains with a set of close by frequencies located within a tolerance range of the desired frequency set.

Also, it can look for combinations of shifts, alternative frequencies, alternative temporal arrangements and/or pulse shape/phase durations of the involved stimulation events.

Furthermore, there may be a search algorithm looking for combinations of shifts and frequency sets avoiding partial or full overlap during a finite duration, of all or some phases of a plurality of multi-phasic pulsed electrical waveforms.

Also, it can look for combinations of shifts and alternative pulse trains.

There may be 3 degrees of freedom, i.e. (time) shift, frequencies and pulse shape or pulse width.

Furthermore, in one example, it is possible that the finite period of time is no longer than 10 second. In another example, the finite period of time is not longer than 1 second. The finite period of time has been identified as on the one hand being sufficiently long for providing a broad range of neurostimulation and achieving the intended effects. Also it is on the other hand sufficiently short enough to reduce complexity for doing the analysis of the pulse trains and to avoid at least partially the overlap of stimulation events.

It is possible that the overlap of stimulation events is completely avoided. This is a very clear and simple rule, which can be implemented and done semi-automatically or automatically. In other words, the method does not allow any overlap of pulses or stimulation events of the first pulse train and the second pulse train (and/or other/further pulse trains).

Pulses may be composed of k phases, with k>1, wherein possible phases of pulses may include but are not limited to stimulation phase, pre-stimulation phase, post-stimulation phase and intra pulse delay phase (or Dip phase).

Furthermore, it should be mentioned that a pulse may also have a single phase. Such a pulse is then named as a monophasic stimulation pulse, with $k \geq 1$.

This can be handled very strictly, i.e. that the stimulation phase and also the pre-stimulation-phase and the post-stimulation phase may not overlap. In other words, there may be a definition that there is no overlap between a certain time frame, e.g. X microseconds or Y milliseconds after and before the pulse. For example, in a multiphasic stimulation, where K>1, stimulation events of a given phase may not overlap with stimulation events of any other phase.

It is also possible that an overlap of the stimulation phase of the pulses is forbidden, which is less strict than a complete and strict avoidance of any overlap. If so, then e.g. the pre-stimulation-phase and the post-stimulation phase may overlap.

Alternatively, an overlap of stimulation events can be partially avoided. For example, an overlap between stimulation pulses may be tolerated for a part of the pulses, e.g. 10% of the pulses of each waveform (or an individual percentage, e.g. 5% of the pulses from the first waveform, 12% of the pulses of the second waveform, etc.).

The frequency tolerance band may be chosen between more or less than 15% of a first frequency defining the first temporal arrangement of stimulation events and/or a second frequency defining the second temporal arrangement of stimulation events, especially more or less than 10% of the first frequency and/or the second frequency. By choosing the tolerance band within such a range it is ensured that still similar or even the same effects of the intended neurostimulation may be achieved.

Moreover, for aperiodic waveforms, it is possible that the tolerance band of a first and/or second instantaneous frequency of a first and/or second aperiodic waveform defining the first temporal arrangement of stimulation events is chosen between more or less than 15% of an average frequency of the first and/or second aperiodic waveform, especially more or less than 10% of a first frequency and/or a second frequency.

There maybe be also more aperiodic waveforms, to which this tolerance band is applied.

The instantaneous frequency is defined as the inverse of the time between 2 subsequent stimulation events or $f\_inst=1/T\ inst$, with $T\_inst=t2-t1$, with t2 the moment that pulse t2 is generated and t1 the moment that the pulse just before that is generated.

The average frequency $f=1/T$ with T the average of all T_inst between subsequent pulses.

It is possible that more than two pulse trains are provided. By this a more sophisticated and complex, but also more effective and more detailed neurostimulation can be provided.

Furthermore, the present invention relates to a system for multi-channel and/or variable neurostimulation. Accordingly, a system for multi-channel and/or variable neurostimulation is provided, at least comprising:

A finite time definition module for defining a finite period of time;

At least one pulse train setter for providing
  a. at least a first pulse train, the first pulse train being provided on a first channel comprising a first temporal arrangement of stimulation events; and
  b. at least a second pulse train, the second pulse train being provided on a second channel comprising a second temporal arrangement of stimulation events;
  c. At least one pulse train analyzer for analyzing the first pulse train and the second pulse train for at least one potential overlap of stimulation events and/or using an analysis whether there is at least one potential overlap of stimulation events of the first pulse train and the second pulse train;
  d. wherein the pulse train setter is configured such that in case of a detected overlap by the pulse train analyzer and/or indicated by the analysis, the first pulse train and/or the second pulse train are adjusted by
  e. Shifting the first pulse train and the second pulse train relatively to each other; and/or
  f. Adapting the first temporal arrangement and/or the second temporal arrangement within a predetermined tolerance band, and/or
  g. Modify at least partially the shape and/or phase duration of the stimulation events of the first pulse train and/or the second pulse train and/or the shape and/or phase duration of at least one phase of a stimulation event being part of the stimulation events of the first pulse train and/or the second pulse train, so as to avoid at least partially the overlap of stimulation events.

The system for neurostimulation can be a transcutaneous system. It can be completely non-invasive.

Alternatively, the system for neurostimulation can be a system that is at least partially implantable or partially implanted (during treatment). Also, it can be embodied such that the system is completely/entirely implantable.

The system can comprise a pulse train setter, e.g. embodied as pulse train setter module.

The pulse train setter module can be located in the implantable part of the neurostimulation system.

However, it is also possible that the pulse train setter module is located in the non-implantable of the neurostimulation system.

The pulse train setter module can be configured such that it computes the necessary adjustments in real-time and/or close to real-time.

In case, that the necessary adjustments are pre-computed, then the pulse train setter module can be embodied as a storage means.

The finite period of time may be no longer than 10 seconds, especially not longer than 1 second.

An overlap of stimulation events may be completely avoided. Implementation embodiments are described above and hereinafter and reference is made to these examples.

Also overlap of stimulation events may be partially avoided. Implementation embodiments are described above and hereinafter and reference is made to these examples.

Furthermore it is possible that the tolerance band is chosen between more or less than 15% of a first frequency defining the first temporal arrangement of stimulation events and/or a second frequency defining the second temporal arrangement of stimulation events, especially more or less than 10% of a first frequency and/or a second frequency.

Moreover, for aperiodic waveforms, it is possible that the tolerance band of a first and/or second instantaneous frequency of a first and/or second aperiodic waveform defining the first temporal arrangement of stimulation events is chosen between more or less than 15% of an average frequency of the first and/or second aperiodic waveform, especially more or less than 10% of a first frequency and/or a second frequency.

There maybe be also more aperiodic waveforms, to which this tolerance band is applied.

The instantaneous frequency is defined as the inverse of the time between 2 subsequent stimulation events or $f\_inst = 1/T\_inst$ with $T\_inst = t2 - t1$, with t2 the moment that pulse t2 is generated and t1 the moment that the pulse just before that is generated.

The average frequency is defined as $f = 1/T$, with T the average of all T_inst between subsequent pulses.

Also, it is possible that more than two pulse trains are provided.

BRIEF DESCRIPTION OF FIGURES

Further details and advantages of the present invention shall now be disclosed in connection with the drawings.

DETAILED DESCRIPTION OF DRAWINGS

Figure 1:
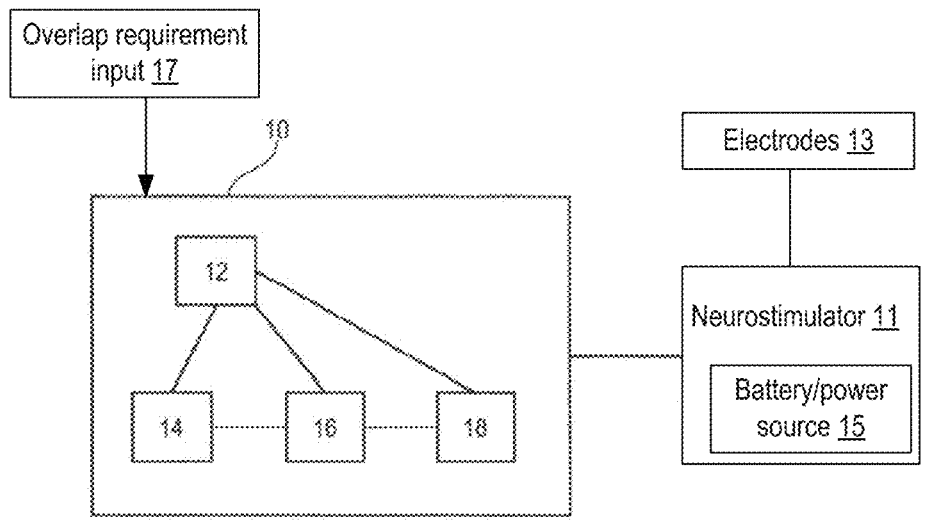
FIG. 1 shows a schematic illustration of an embodiment of a system for multi-channel and/or variable neurostimulation, with which the method according to the present invention can be performed.

FIG. 1 shows a schematic overview of an embodiment of a system 10 for multi-channel and/or variable neurostimulation, with which the method according to the present invention can be performed.

The system 10 comprises a controller 12 which is capable to control the components and modules as specified below. In particular, the controller 12 through its processors and controllers, may adjust the operation and function of the system 10. As an example, the controller 12 may adjust operation of a finite time definition module 14, a pulse train setter 16, and a pulse train analyzer 18 of system 10. Further, the controller 12 may receive one or more inputs, and adjust operation of one or more components of the system 10 based on the received inputs. As an example, the controller 12 may receive an overlap requirement input 17, from a user via a user interface included in or coupled to the system 10. Based on the overlap requirement input 17, the controller 12 may adjust operation of the finite time definition module 14, the pulse train setter 16, and the pulse train analyzer 18 to define a period of time for overlap analysis, perform overlap analysis, and generate one or more modified pulse trains, where the one or more modified pulse trains have overlap based on the overlap requirement input 17. The one or more modified pulse trains may be utilized to provide stimulation to a patient via a lead comprising a plurality of electrodes, such as electrodes 13. The controller 12 may also control how information, including data acquired during the operation of the system 10, is processed, displayed, stored, and manipulated. The different processing steps, including receiving one or more signals from one or more sensors, receiving user input, evaluating the received signals/input, adjusting one or more components of the system 10 to control operation of the system 10, including the methods described herein, performed by the controller 12, may be provided by a set of instructions stored in non-transitory memory of the processor. Information may also be stored in one or more non-transitory memories of controller 12 for later retrieval and use.

The system 10 comprises the finite time definition module 14 for defining a finite period of time.

Furthermore, the system 10 includes at least one pulse train setter 16.

The pulse train setter 16 is configured and arranged for providing
 a. at least a first pulse train, the first pulse train being provided on a first channel comprising a first frequency of stimulation events; and
 b. at least a second pulse train, the second pulse train being provided on a second channel comprising a second frequency of stimulation events.

A pulse train in the sense of this disclosure and this example embodiment is to be understood as a finite time period with one or more stimulation events such as at least one stimulation pulse or stimulation burst. These events are occurring according to the embodiment of the present invention within the (chosen) finite period of time. A pulse train in the sense of this invention may have its own inter and intra burst frequency and may be provided on a (neurostimulation) channel.

There can be two pulse trains or as shown in some examples, three or even more pulse trains. Additionally, there is at least one pulse train analyzer 18. The pulse train analyzer 18 is configured and arranged for analyzing the first pulse train and the second pulse train for at least one potential overlap of stimulation events.

The pulse train analyzer 18 is configured and arranged to detect overlap in the pulse trains. The pulse train setter 16 is configured such that in case of a detected overlap, the first pulse train and/or the second pulse train are adjusted by
 a. Shifting the first pulse train and the second pulse train relatively to each other; and/or
 b. Adapting the first frequency and/or the second frequency within a predetermined tolerance band, and/or
 c. Modify at least partially the shape and/or phase duration of the first pulse train and/or the second pulse train and/or the shape and/or phase duration of at least one pulse being part of the first pulse train and/or the second pulse train, so as to avoid at least partially the overlap of stimulation events.

The finite period of time in the system 10 is no longer than 10 seconds. Special setups may have setups, where the finite period of time is no longer than 1 second.

As shown below, the system 10 can be arranged and configured such that an overlap of stimulation events is completely avoided and/or that an overlap of stimulation events is partially avoided.

Also, the system 10 is arranged and configured such that the tolerance band is chosen between more or less than 15% of the first frequency and/or the second frequency. In one example, the tolerance band may be chosen between more or less than 10% of the first frequency and/or the second frequency.

The system 10 can be coupled or be part of a neurostimulator 11. The neurostimulator 11 may be an implantable pulse generator (IPG), which can be implanted and connected with electrodes 13 or an electrode paddle. In one example, the neurostimulator 11 may be configured to provide stimulation to a patient via a lead comprising a plurality of electrodes.

An example method performed with the system 10 and functionality of the system 10 is discussed below. A high-level flowchart illustrating an example method that may be implemented with system 10 for detecting an overlap, such as overlap of stimulation events, between at least two pulse trains is described further below with respect to FIG. 16.

Figure 2:
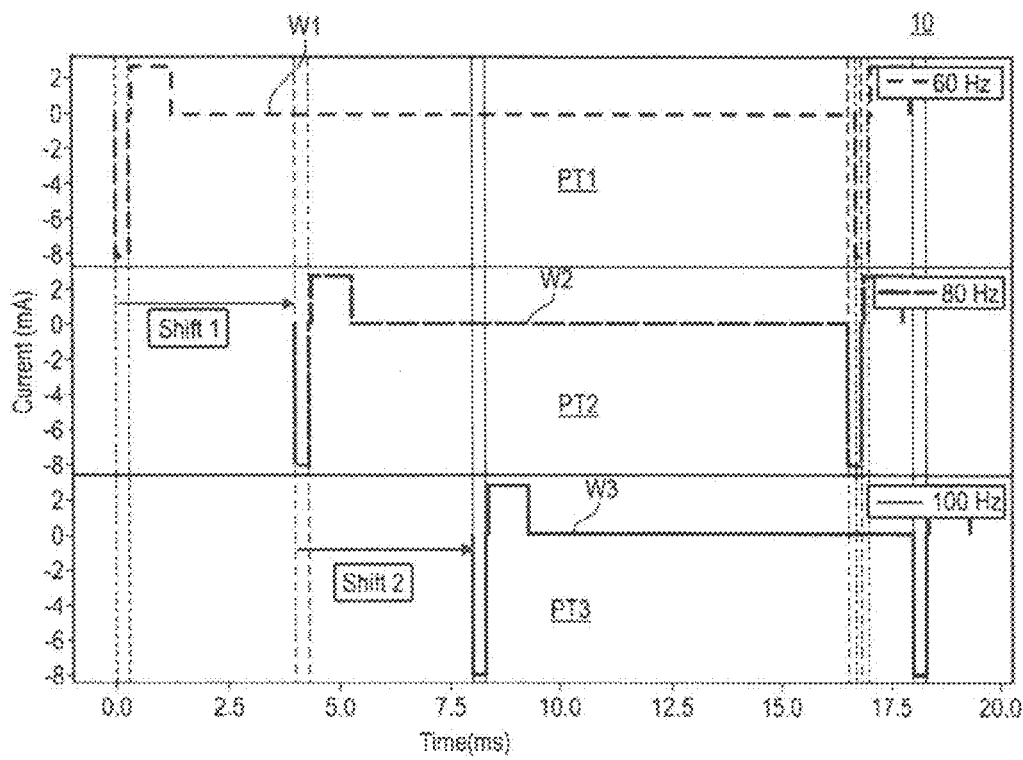
FIG. 2 shows a graph illustrating an example of triphasic waveforms with identical phases at f=(60, 80, 100) Hz with an equal shift of 3 milliseconds (ms) between the timing channels.

The example method implemented and performed with the system 10 to avoid overlap of pulses of three pulse trains PT1, PT2, PT3 between the electrical waveforms adds a delay between each of the electrical waveforms, called shift (c.f. FIG. 2, which shows 3 triphasic waveforms W1, W2, W3 with identical phases at f=(60, 80, 100) Hz with an equal shift of 3 ms between the timing channels) and replaces the desired frequency set from these electrical waveforms with a set of close-by frequencies located within a tolerance range from the desired frequency set. For example, a tolerance of 10% on a 60 Hz desired frequency waveform may result in a realized frequency between 54 Hz and 66 Hz. In each of the graphs shown herein, including at FIGS. 2-6, and 8-15, the X-axis represents time in milliseconds (ms) and the Y-axis represents Current in milliAmperes (mA).

Figure 3:
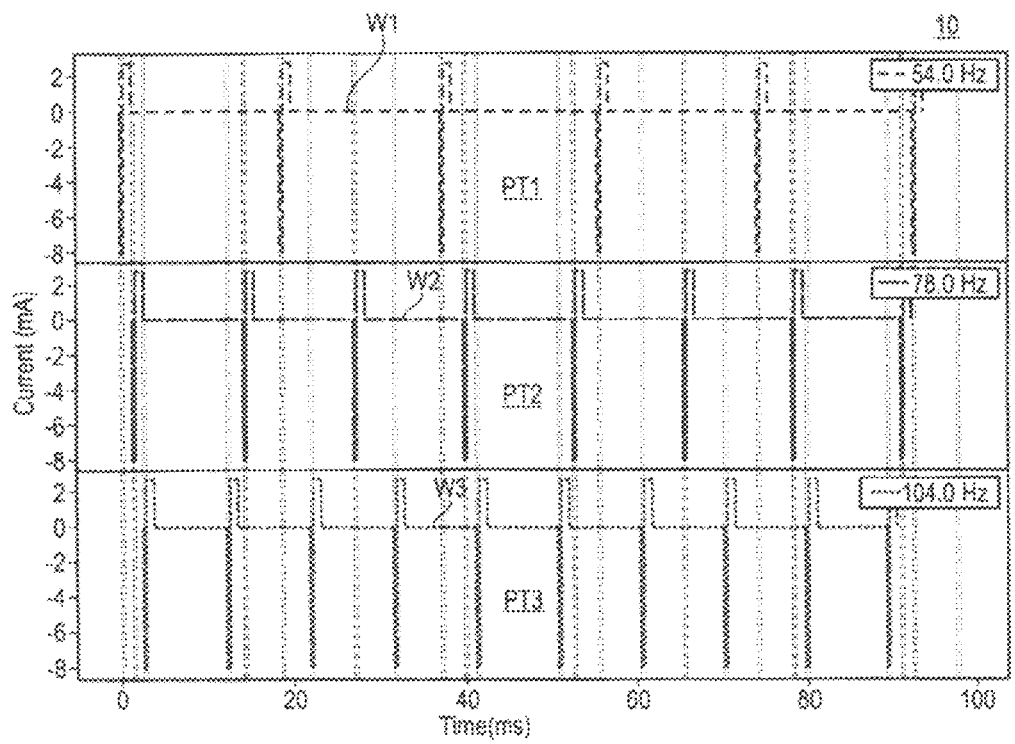
FIG. 3 shows a graph illustrating an example solution avoiding full overlap for the set of triphasic waveforms with identical phases at f=(60, 80, 100) Hz; composed of a 1.3 ms shift and of the frequencies (54, 78, 104) Hz.

The method and the system 10 can perform a search algorithm looking for combinations of shifts, of frequency sets, and/or of alternative pulse shapes avoiding partial or full overlap, of all or of some of the phases, during a finite duration, for a plurality of multiphasic pulsed electrical waveforms, which are called solutions (c.f. FIG. 3). The search method can be used either to find one solution or a complete set of solutions. The finite duration during which overlap is avoided generally matches the duration of the functional muscle block involved in the overlap or the duration of a segment in a gait-cycle. The algorithm can be used to find solutions for larger time scales.

Figure 4:
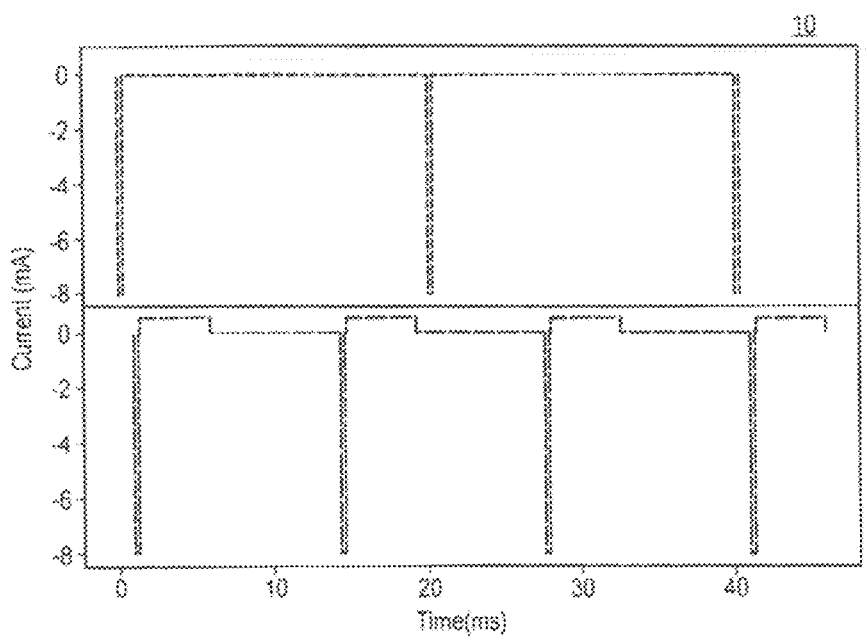
FIG. 4 shows a graph illustrating an example of 2 waveforms, monophasic and multiphasic, at the frequencies f=(50, 75) Hz.

In FIG. 3, all the waveforms W1, W2, W3 are triphasic: stimulation phase, intra pulse delay phase (or Dip), post-stimulation phase (a ratio of 3 between post-stimulation and stimulation timing/currents is chosen in FIG. 3). Moreover, all these phases have the same duration between waveforms: 300 µs for the stimulation phase, 50 µs for the Dip and 900 µ5s for the post-stimulation phase. FIG. 4 shows two waveforms, wherein one of them is monophasic. This method is not limited to a plurality of waveforms with the same number of identical phases. It can be applied to waveforms with a different number of phases, and with different phases duration between waveforms. It can even be applied to aperiodic waveforms, cf. FIG. 14 and FIG. 15.

Figure 5:
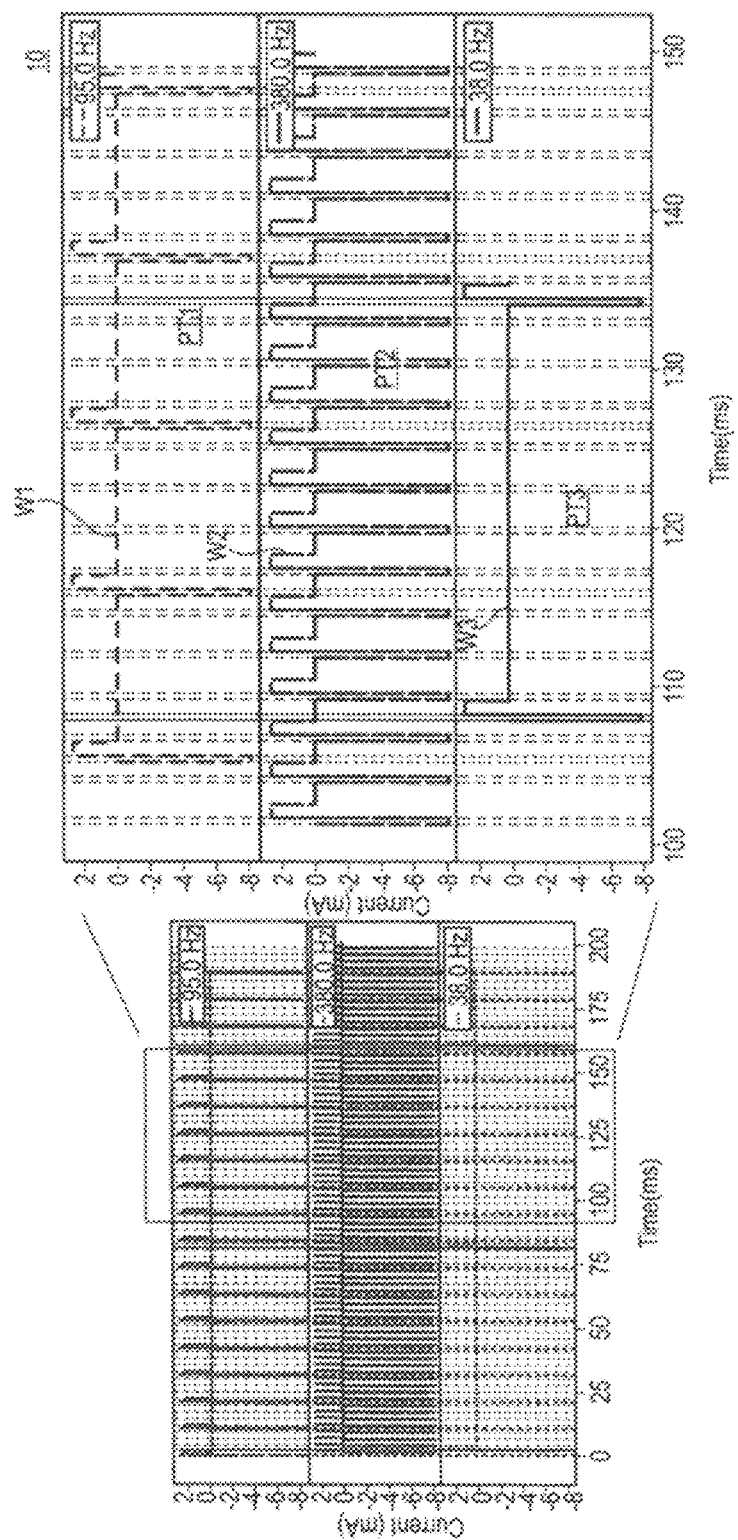
FIG. 5 shows a graph illustrating a solution for the desired set of triphasic waveforms with identical phases with the frequencies (100, 400, 40) Hz; composed of a 1.3 ms shift and of the frequency set (95, 380, 38) Hz.

An example of such waveforms is given in FIG. 5 showing a solution for the desired set of triphasic waveforms with identical phases with the frequencies (100, 400, 40) Hz, composed of a 1.3 ms shift and of the frequency set (95, 380, 38) Hz.

The example in FIG. 5 shows, how full overlap is avoided with a frequency tolerance of 10% for 3 triphasic waveforms with identical phases whose desired frequency set is (100, 400, 40) Hz. The solution provided uses a 1.3 ms shift together with the realized frequency set (95, 380, 38) Hz. Note that this solution uses an equal shift between all waveforms.

This method can also be applied to avoid overlapping of specific phases from each of the waveforms.

Figure 6:
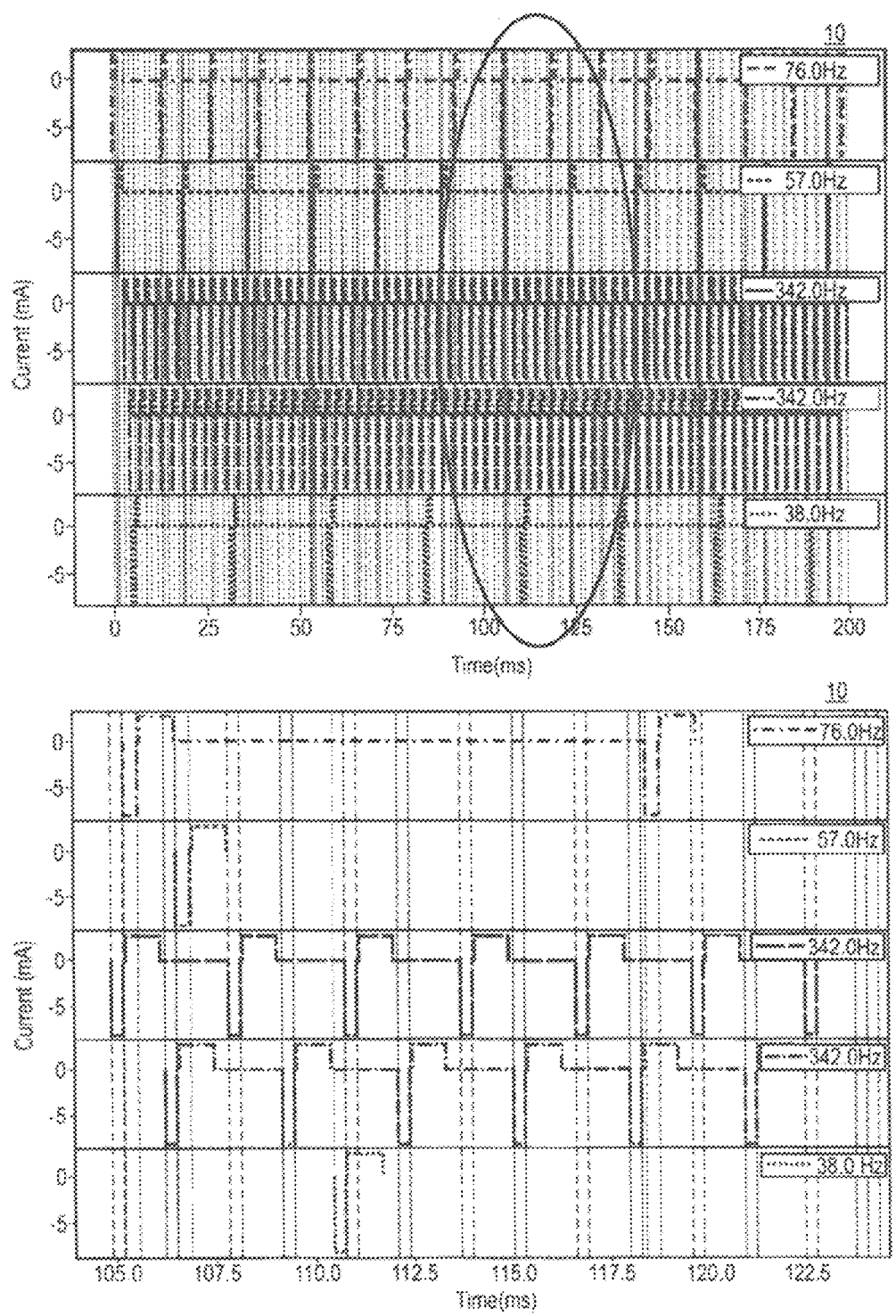
FIG. 6 shows a graph illustrating a solution for the desired set of triphasic waveforms with identical phases with the frequencies (80, 60, 350, 350, 40) Hz where only the first phase overlap is avoided.
Figure 7:
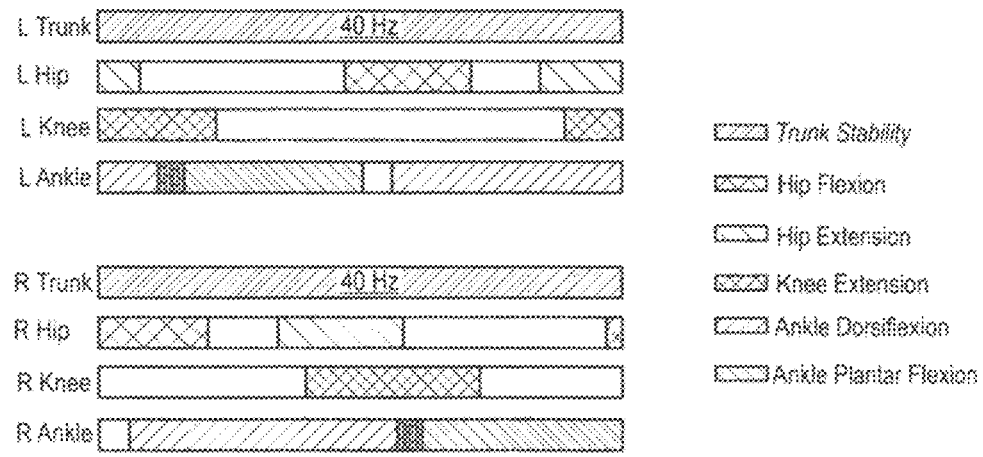
FIG. 7 shows a schematic illustration of a possible stimulation program without the frequencies and amplitudes for a gait cycle.
Figure 8:
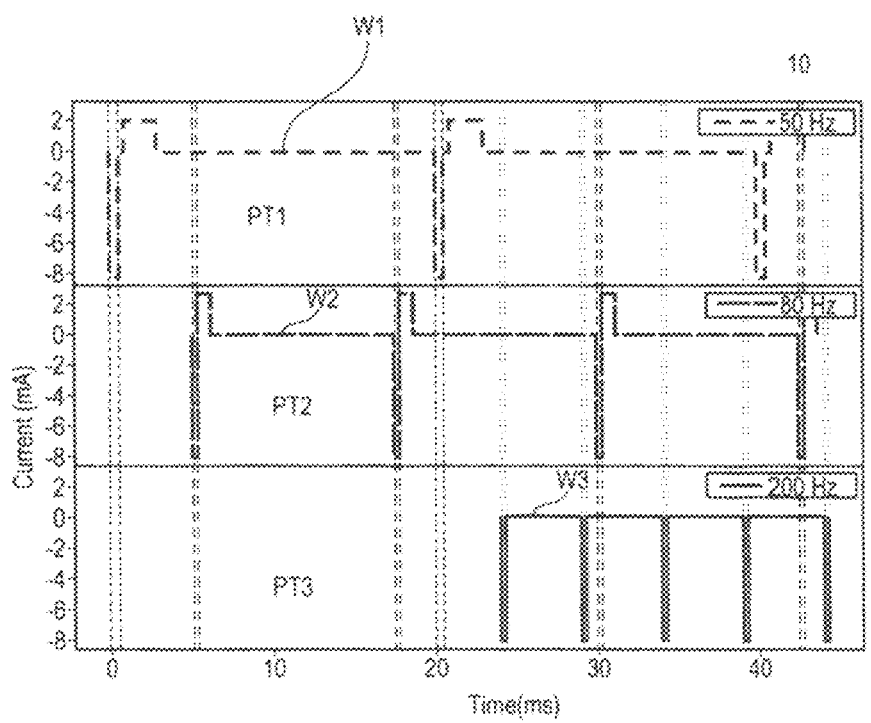
FIG. 8 shows a graph illustrating an example of several pulse trains each comprising possible pulsed electrical waveforms between 0 and 50 ms.

An example is provided FIG. 6 where the solution only avoids overlap of the first phase (stimulation phase) from the pulse of each waveform while it tolerates overlap of the first phase from a pulse of one waveform with the second or third phase from a pulse of another waveform. This method can be used either to compute on-the-fly (i.e. online) a solution or to precompute (i.e. offline) a look-up table with one or several solutions stored for most or every occurring scenario of overlapping that is encountered for the different rehabilitation exercises like walk training. The look-up table may be stored in non-transitory memory of a controller, such as controller 12. This look-up table can then be used by a second algorithm looking at the complete stimulation program and determining if the desired electrical waveforms must be replaced by the corresponding solutions stored in the look-up table. As an example, a stimulation program using a plurality of functional muscle blocks (FMBs) at the same time is provided in FIG. 7. In particular, FIG. 7 shows a possible stimulation program without the frequencies and amplitudes for a gait cycle, the shown partiture using 12 FMBs). For example, an FMB determines an electrode configuration, an amplitude/intensity of stimulation and a pulse train comprising a temporal arrangement of stimulation events. Thus, during movement, e.g. a gait cycle, different FMBs need to be stimulated simultaneously with different pulse trains (that is, pulsed electrical waveforms) at different frequencies and amplitudes, sometimes with different pattern of pulses, in order to reproduce a movement, e.g. cycle comparable to a healthy subject. The different pulse trains simultaneously stimulating different FMBs may be evaluated for desired overlap (e.g., avoiding overlap of first phase, while tolerating overlap of the first phase from a pulse of one waveform with a second or third phase from a pulse of another waveform as discussed at FIG. 6 above)

This approach is most suited for open-loop (offline) use but can also be implemented in closed-loop (online) scenarios in which stimulations parameters are updated. For example, the updated stimulation parameters might be the frequency of a used functional muscle block (FMB), as well as its temporal start position and duration within the stimulation program. The proposed method could then be reapplied to the updated stimulation settings to determine if the desired electrical waveforms are in accordance to the required overlapping criteria, and if not, adapt the stimulation program with and/or for one or several solutions that might, for example, be taken from the look-up table. The look-up table may also be updated to include additional solutions for the various scenarios stored in the look-up table, and may also be updated to include new scenarios corresponding to new rehabilitation regimens.

This method can be applied in all kind of other ways. For example, the algorithm can be set to avoid overlap of more than a certain amount of tolerated overlap or allow a single overlap between a post-stimulation and stimulation phase of two different FMBs. In this scenario, a metric is computed to quantify the amount of overlap and used as criterion for the solution selection within the algorithm.

In a possible embodiment of a neurostimulation system, this system 10 and method would apply to avoid overlap of the pulses delivered by an IPG being part of the neurostimulation system. For a low-frequency range, this algorithm might completely avoid overlap of pulses (of both stimulation and post-stimulation parts); while for a higher frequency range, some overlap flexibility might be tolerated. For example, the overlap of a stimulation with a post-stimulation phase, or a certain amount of pulse overlap might be tolerated. An insight on the degree of allowable tolerance might be determined through neuronal spinal cord simulations.

The goal of method and system according to the present disclosure is to schedule as many pulses as possible on the timeline without endangering the patient safety and without reaching the hardware limits. Moreover, this method is not limited to spinal cord neurostimulation and can be applied to any type of neurostimulation such as Deep Brain Stimulation (DBS).

The disclosure can be used for paddle and percutaneous leads, transcutaneous electrical nerve stimulation (TENS), and all neurostimulation and muscle stimulation applications that use more than one electrode, and/or more than one lead.

This present disclosure can also be used for paddle and percutaneous leads, transcutaneous electrical nerve stimulation (TENS), and all neurostimulation and muscle stimulation applications that use more than one electrode, and/or more than one lead.

The input is composed of n pulsed electrical waveforms. For example, for n=3, W1, W2, W3 of three pulse trains PT1, PT2, PT3, monophasic or multiphasic, outputted during a finite duration between $t_0$ and $t_f$. For instance, the input could be the 3 waveforms in FIG. 8. between 0 and 45 ms. The first one is a triphasic waveform (500+400+2 000 µs phases) at the frequency 50 Hz; the second one is a biphasic waveform (300+1200 µs phases) at the frequency 80 Hz and starting 5 ms after the first one; and the third one is a monophasic waveform (300 µs phase) at the frequency 200 Hz and starting 24 ms after the first one.

The method takes the input and introduces slight changes in such a way that the pulsed electrical waveforms respect validation conditions between $t_0$ and $t_f$. First, the method adds a "shift" called $d_{shifti}$: it's an initial delay between the individual waveforms. The shift delays the first pulse of the waveform from $t_0$ to $t_0 + d_{shifti}$ where "i" is the number of the waveform. This initial delay comes from an obvious statement: if the pulsed electrical waveforms starts simultaneously with each of their first pulse outputted at $t_0$, then all their first pulses will overlap. This is an example for a shifting relatively to a fix point in time.

Figure 9:
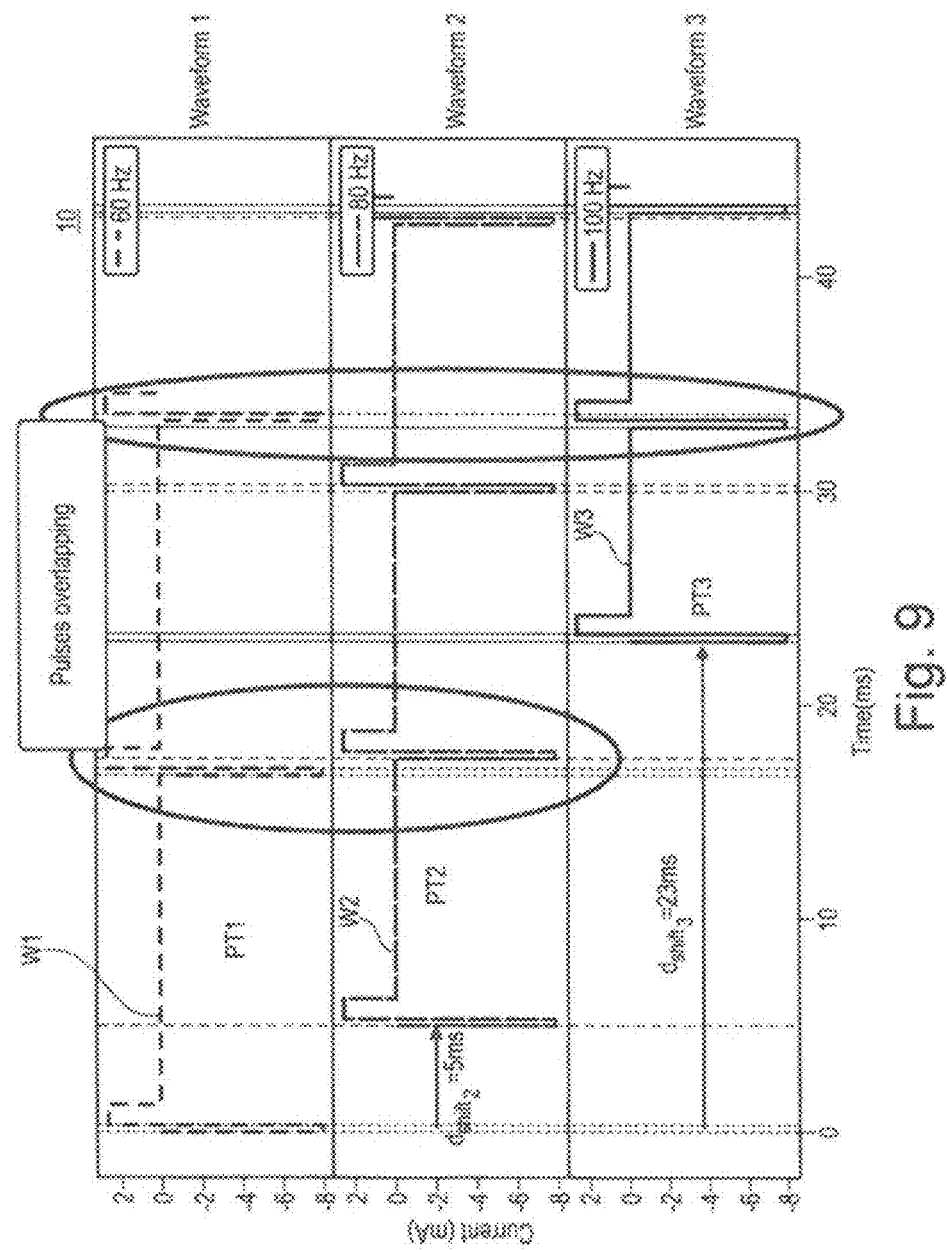
FIG. 9 shows a graph illustrating an example of overlapping pulse trains.

In the example FIG. 9, the first waveform W1 of pulse train PT1 does not have any shift and starts at $t_0 = 0$ ms, while the two others W2 and W3 of pulse trains PT2, PT3 respectively have a shift of 5 and 23 ms respectively, delaying each of their first pulse. The chosen shifts do not avoid overlapping of the pulses. The shifts are not necessarily equal between every waveform. However, for the following figures and examples in this document, it will be assumed as equal and the notation shift=x ms will mean that the first pulse of waveform n is delayed by x ms with respect to the first pulse of waveform n−1. This choice was made to limit the computational impact of the method, and to reduce the computational time required.

The method also implements several types of modification on each of the waveforms:

Modification of the frequency within a requirement range: the frequency should be realized with a certain accuracy. An 80 Hz waveform with a 10% variation allowed could become a 78 Hz waveform or an 88 Hz waveform.

Modification of the duration of the phases: each phase could have its duration individually modified. For instance, a triphasic waveform with third phase width of 1200 us could have its third phase duration limited to 900 us. Once chosen, every modification applied to the pulsed electrical waveform is kept fixed between $t_0$ and $t_f$.

Finally, the method tests each combination of shift and modified waveform during the finite duration $t_f - t_0$ and saves the combinations that meets predefined conditions during this duration. The combinations matching these conditions are called "solutions" and form the solution space for a given input and for a desired set of boundary conditions.

The possible conditions: The most obvious condition that could be checked concerns the temporal overlap of the pulses of the pulse trains PT1, PT2, PT3. Let's first consider a scenario where overlap of the pulses is forbidden with a 10% frequency variation allowed. An input combination of 3 biphasic waveforms with identical phases (300+900 µs) at the frequencies (60, 80, 100) Hz between $t_0$ and $t_f$ could become a combination of 3 triphasic waveforms with the same phases at the frequencies (54, 78, 104) Hz with a shift of 1.3 ms, such as represented in FIG. 3, showing a solution avoiding full overlap for the set of biphasic waveforms with identical phases at f=(60, 80, 100) Hz composed of a 1.3 ms shift and of the frequencies (54, 78, 104) Hz.

Figure 10:
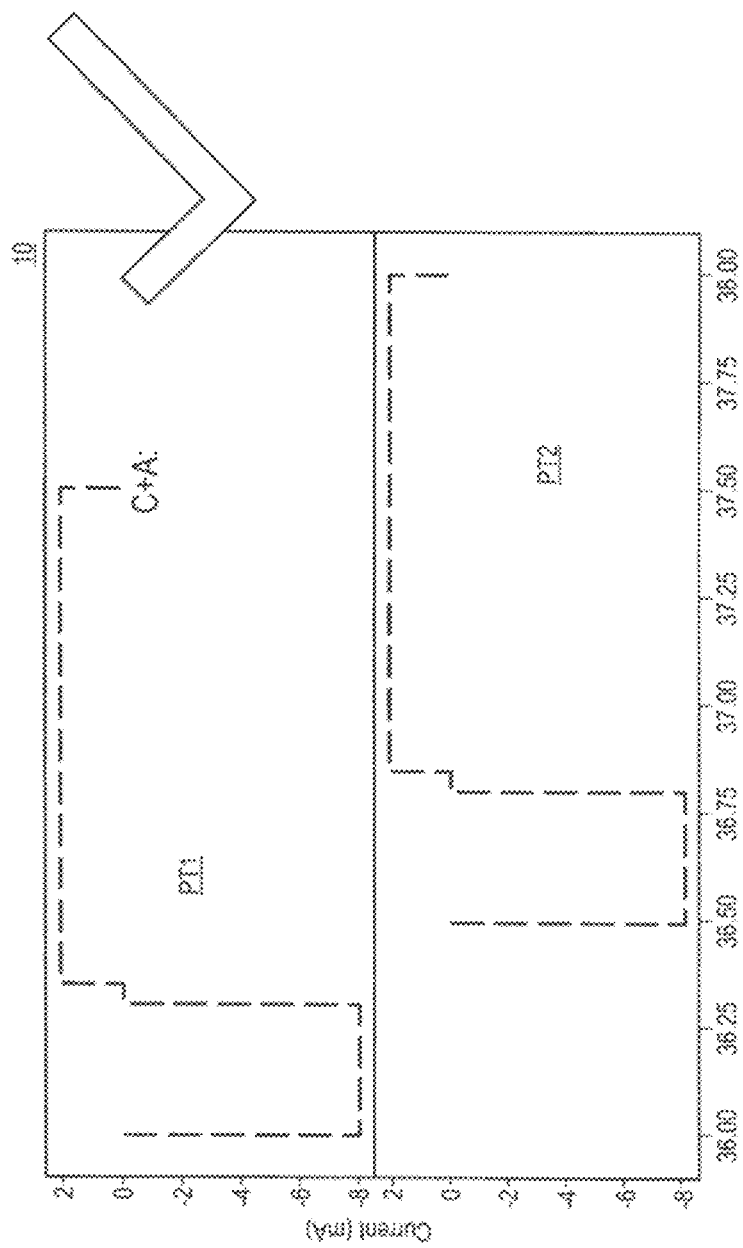
FIG. 10 shows a graph illustrating an example solution allowing partial overlap of pulse trains.

FIG. 10 shows a diagram with an example solution allowing partial overlap of pulse trains PT1 and PT2.

Figure 11:
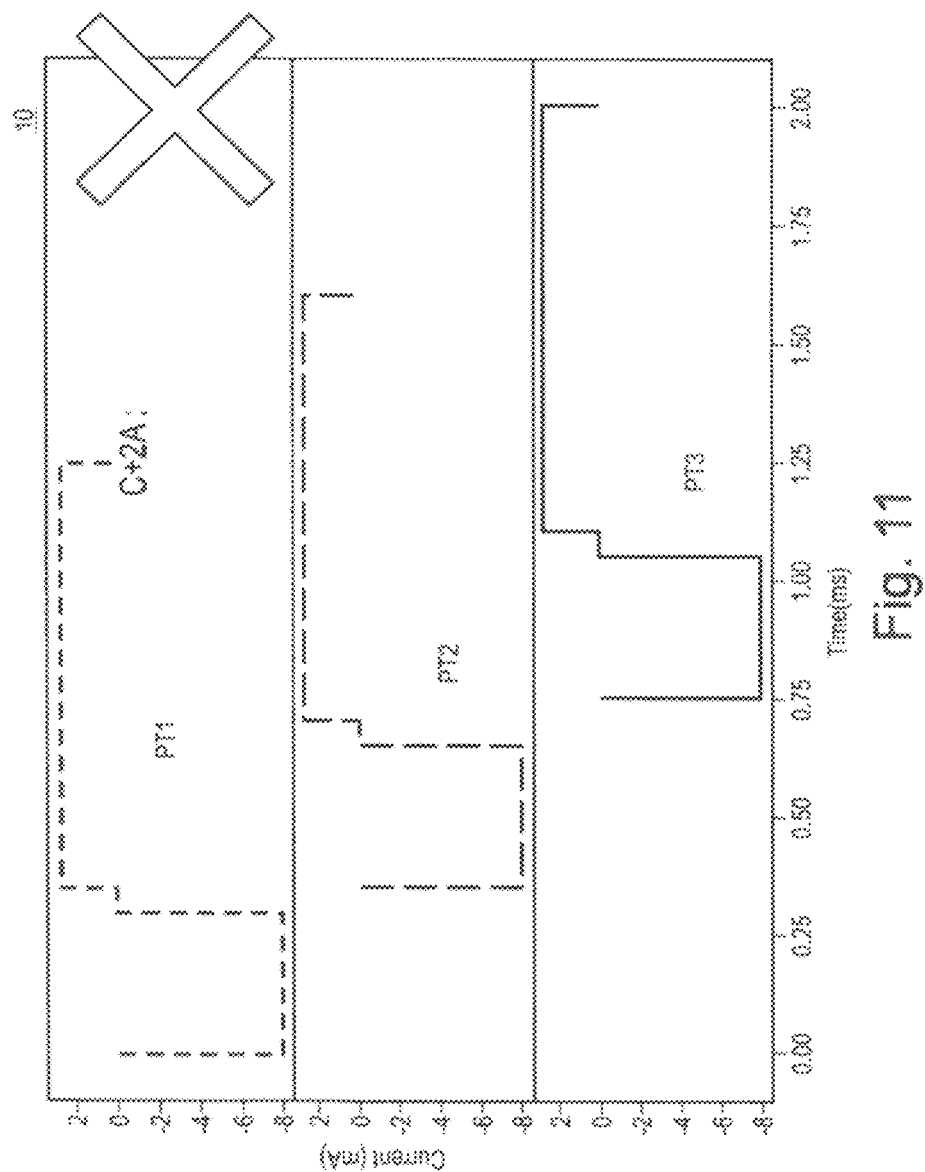
FIG. 11 shows a graph illustrating an example solution not allowing partial overlap of pulse trains.

FIG. 11 shows a diagram with an example solution not allowing partial overlap of pulse trains PT1, PT2 and PT3.

Generally speaking, the user could define the overlap requirement in different ways:
a. Overlap between pulses is forbidden (strict)
b. Overlap between stimulation phase of the pulses is forbidden (not as strict, post-stimulation phase can overlap with a stimulation phase)
c. Overlap between pulses is tolerated for 10% of the pulses from each waveforms (or individual percentages, e.g. for 5% of the pulses from the first waveform, 12% of the pulses from the second waveform, etc.)

For example, an approach can be used where the overlap requirement allows 1 stimulation pulse from a burst train to overlap with the post-stimulation phase of a continuous waveform. This allowable combination is shown in the lower figure in FIG. 10.

Additionally, the algorithm can count the number of post-stim phases with which the stimulation phase is overlapping. In the just mentioned overlap requirement, the stimulation phase of the bottom waveform PT2 overlaps with 1 post-stim phase from the top waveform PT1. However, in the case shown in FIG. 11, this overlap requirement is violated, because although the top 2 waveforms PT1 and PT2, respectively, are similar to the waveforms in the lower figure in FIG. 10, the bottom waveform PT3 has its stimulation phase overlapping with 2 post-stimulation phases violating the overlap requirement.

This last point can be generalized as follows: an overlap requirement can state that a specific phase from a given waveform can overlap with specific phases from n other waveforms.

Figure 12:
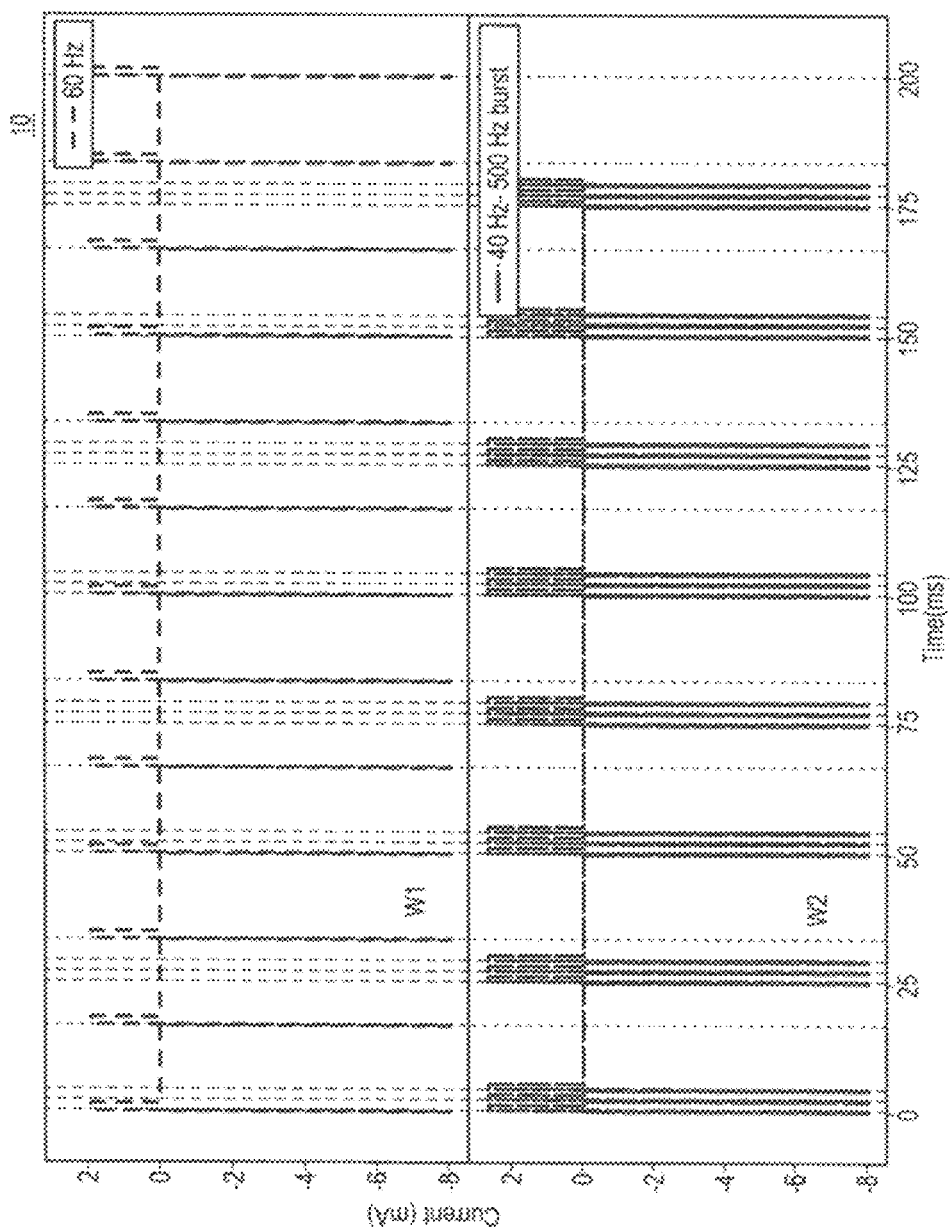
FIG. 12 shows a graph illustrating example continuous waveform and burst waveform without pulse train shifting.

FIG. 12 shows two desired waveforms, i.e. waveform W1 and waveform W2. W1 is a 60 Hz continuous waveform with triphasic pulses (300 µs stimulation, 50 µs Dip, 1250 µs post-stimulation). W2 is a burst waveform with a 40 Hz inter burst frequency using triplets of triphasic pulses (300 µs stimulation, 50 µs Dip, 1250 µs post-stimulation) and an intra burst frequency of 500 Hz. As can be seen in FIG. 12, without pulse train shifting, an overlapping occurs every 50 ms.

Figure 13:
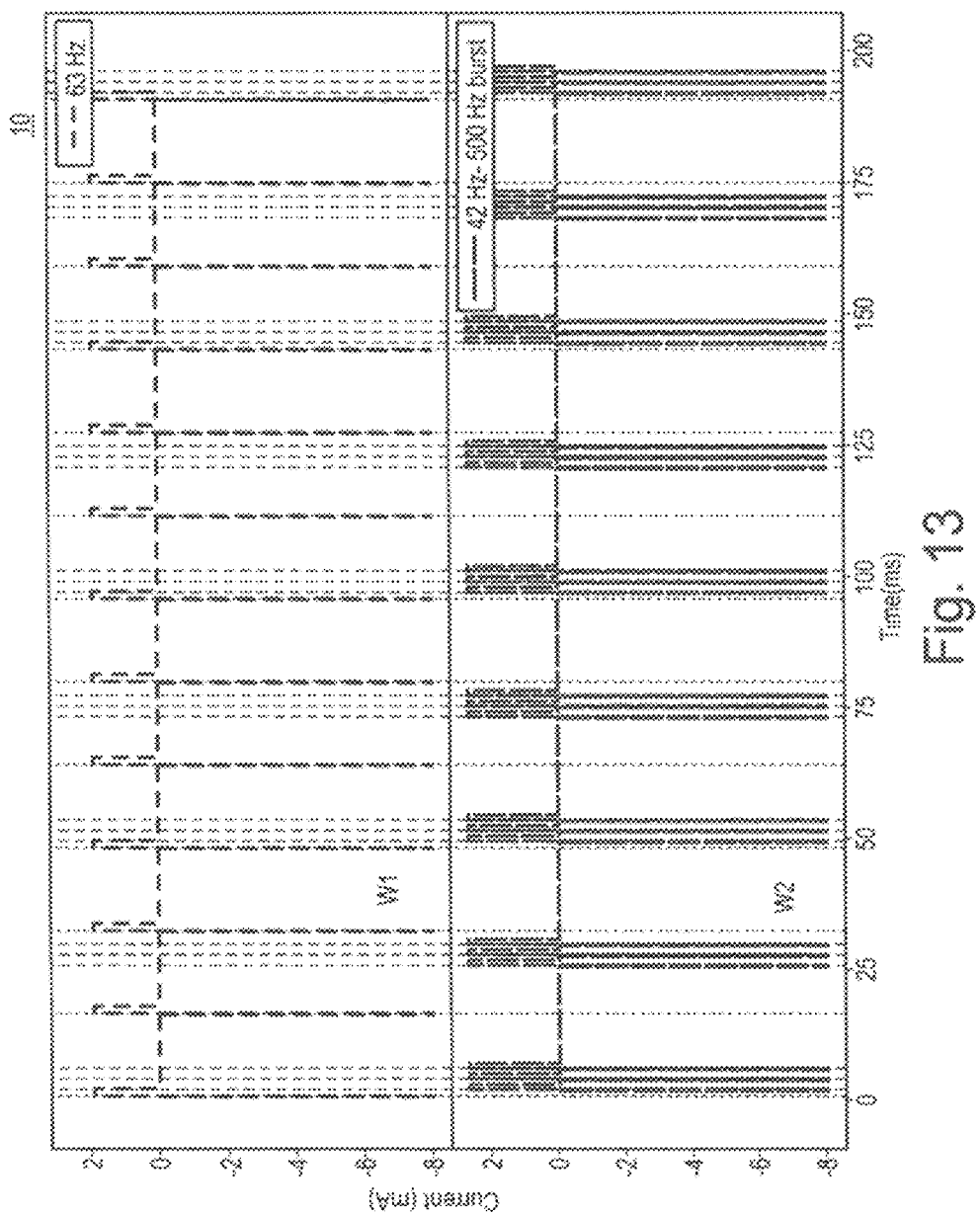
FIG. 13 shows a graph illustrating example continuous waveform and burst waveform with pulse train shifting.

According to the invention, i.e. with pulse train shifting, one solution could be as shown in FIG. 13: The first waveform W1 is shifted from an inter burst frequency of 60 Hz to 63 Hz. Furthermore, the burst waveform W2 is shifted from an inter burst frequency of 40 Hz to 42 Hz with a shift of 1.50 ms. The intra burst frequency is still 500 Hz for both waveforms. With this solution, no overlapping will occur anymore (within the shown time frame).

It should be noted that for burst waveforms, solutions could also involve changing the intra burst frequency within a predetermined tolerance band.

Figure 14:
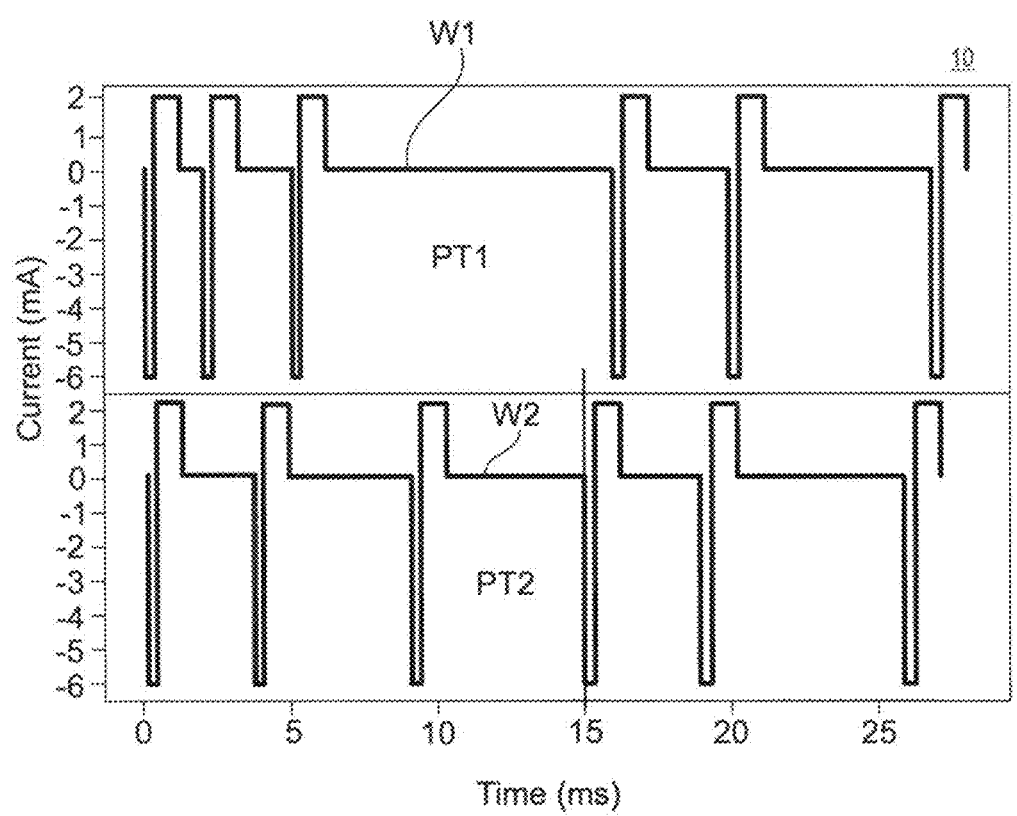
FIG. 14 shows a graph illustrating an example of two partially overlapping aperiodic waveforms, without pulse train shifting.

FIG. 14 shows an example of two partially overlapping aperiodic waveforms, without pulse train shifting.

The first waveform W1 and the second waveform W2 both are aperiodic waveforms.

The pulse trains PT1 and PT2 overlap partially.

Figure 15:
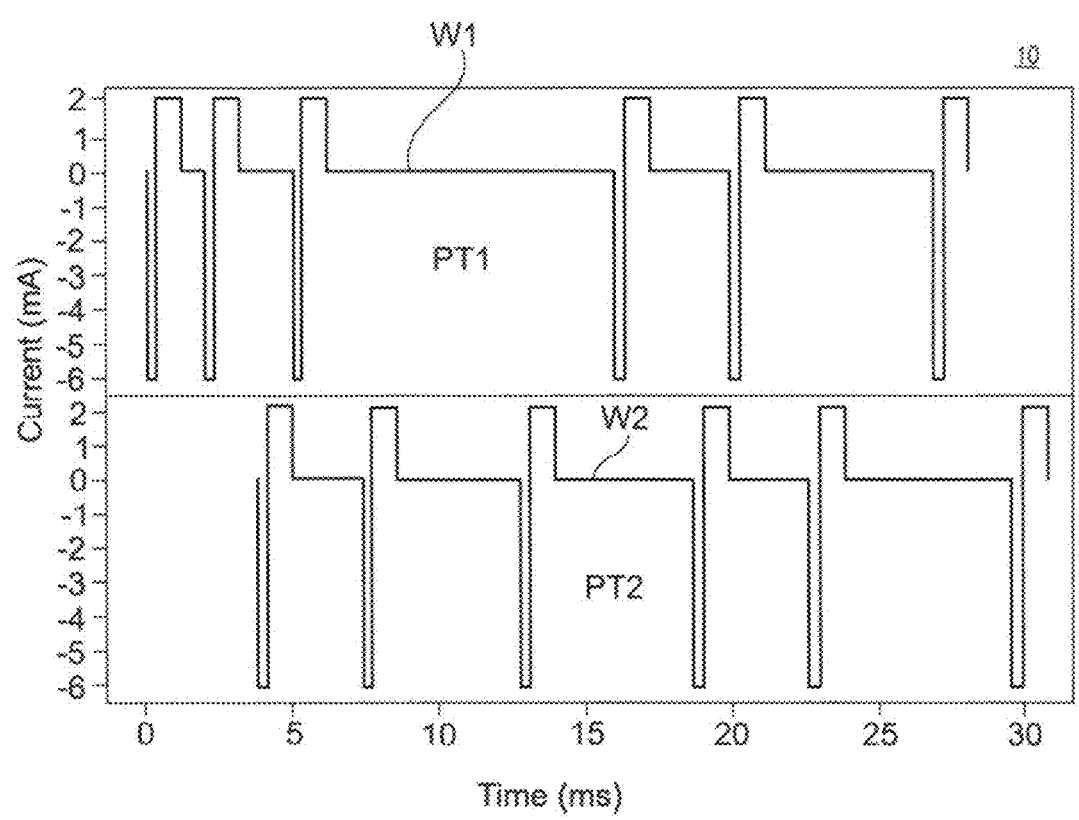
FIG. 15 shows a graph illustrating an example solution avoiding overlap of two aperiodic waveforms, composed of a 3.5 ms shift.

The overlap could be avoided by adding a delay between the waveforms W1 and W2, i.e. shifting one waveform, cf. FIG. 15, where overlap of two aperiodic waveforms is avoided by a 3.5 ms shift of W2.

Figure 16:
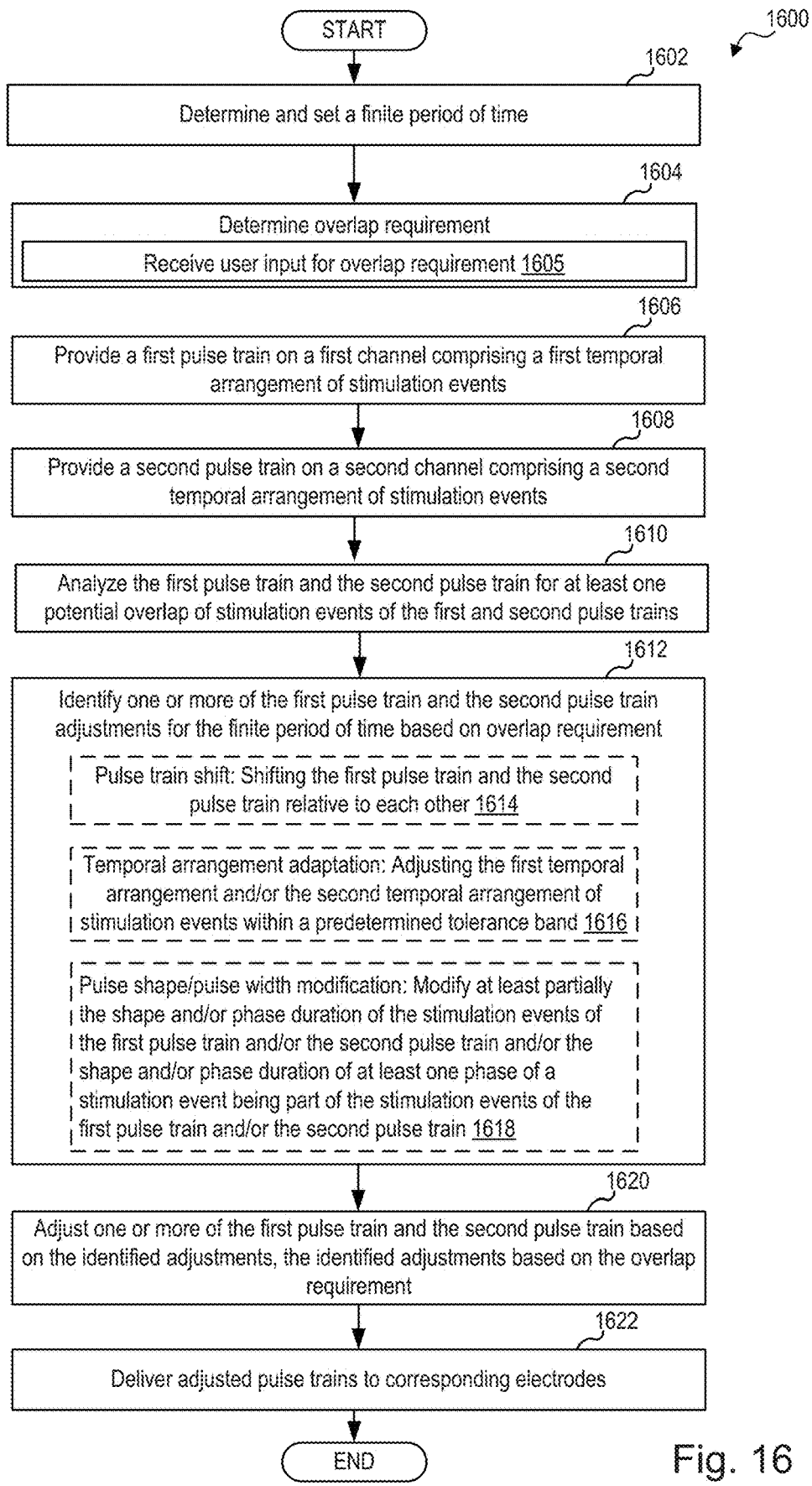
FIG. 16 shows a graph illustrating an example method for modifying one or more parameters of one or more pulse trains in order to reduce overlap of stimulation events between two or more pulse trains.

FIG. 16 shows a high-level flow chart illustrating an example method 1600 for modifying one or more parameters of one or more pulse trains in order to reduce overlap of stimulation events between two or more pulse trains. While the method 1600 below is described with respect to two pulse trains, it will be appreciated that the method 1600 may be implemented for evaluating and modifying a plurality of pulse trains (that is, pulse electrical waveforms). Further, while the present method 1600 is described for open-loop control, the method 1600 may be modified to achieve closed loop control in which responsive to modification of stimulation parameters, the modified waveforms may be evaluated based on the overlap requirement, and if not met, one or more solutions may be determined. Method 1600 may be implemented by a processing system, such as controller 12 at FIG. 1, or one or more processing systems in communication with the processing system, or any appropriate combination thereof. Further, the method 1600 may be implemented by controller 12 in conjunction with modules and components of system 10, such as finite time definition module 14, pulse train setter 16, and pulse train analyzer 18. It will be appreciated that the controller 12 may be configured include the finite time definition module 14, pulse train setter 16, and pulse train analyzer 18, and such a configuration is within the scope of the disclosure. Furthermore, in some examples, one or more modules and components of system 10, such as the pulse train analyzer 18, may be configured to implement the method 1600 based on instructions stored in non-transitory memory, in conjunction with other modules of the system, such as pulse train setter 16 and finite time definition module 14. Method 1600 is described with regard to the systems and components of FIG. 1, although it should be appreciated that method 1600 may be implemented with other systems and components without departing from the scope of the present disclosure.

At 1602, the method 1600 includes determining and setting a finite period of time. The finite period of time may be a finite time duration during which two or more pulse trains are analyzed for overlap. The finite period of time may be sufficiently long for providing a broad range of neurostimulation and achieving the intended effects while being sufficiently short enough to reduce complexity for doing the analysis of the pulse trains and to avoid at least partially the overlap of stimulation events.

In one example, the finite period of time is no longer than 10 second. In another example, the finite period of time is no longer than 1 second.

By only looking at a finite period of time, collisions or overlap events may be recognized and be found in this finite time period and thus, the need to find and avoid such events outside of such period is reduced. As a result, improved control of the neurostimulation may be achieved.

In one example, the finite definition module may be determined and set by finite time definition module 14 at FIG. 1. In another example, upon determining the finite period of time, the controller 12 may command the finite time definition module 14 to set the finite period of time.

Next, 1604, the method 1600 includes determining an overlap requirement. In one example, the requirement may be strict. For example, overlap between pulses may be forbidden. In another example, overlap between stimulation phase of pulses may be forbidden. For example, post-stimulation phase a pulse may overlap with a stimulation phase of another pulse. In yet another example, overlap may be tolerated for a percentage of pulses from each waveforms (e.g., 5% of pulses from one waveform, 10% of pulses from another waveform). In another example, a specific phase from a given waveform can overlap with specific phase from "n" other waveforms, where n=1, 2, 3, . . . etc.

In another example, the overlap requirement may be based on frequency of pulse trains. For example, for a low-frequency range, overlap of pulses (of both stimulation and post-stimulation parts) may be completely avoided; while for a higher frequency range, some overlap flexibility might be tolerated. For example, the overlap of a stimulation with a post-stimulation phase, or a certain amount of pulse overlap might be tolerated. An insight on the degree of allowable tolerance might be determined through stimulations, such as neural spinal cord stimulation, deep brain stimulation, etc., for example. Accordingly, in some examples, the overlap requirement or overlap tolerance may be based on the functional muscle blocks stimulated.

Further, in some examples, as indicated at 1605, a user may specify the overlap requirement via a user interface coupled to the system 10.

Next, at 1606, the method 1600 includes providing a first pulse train comprising a first arrangement of stimulation events, and at 1608, the method 1600 includes providing a second pulse train comprising a second arrangement of stimulation events. For example, the first pulse train and the second pulse train may be provided via a pulse train setter, such as pulse train setter 16 at FIG. 1.

Next, at 1610, the method 1600 includes analyzing the first pulse train and the second pulse train for at least one potential overlap of stimulation events of the first and second pulse trains within the finite time period. That is, the analysis of the first pulse train and the second pulse train for overlapping events is not performed for other time periods outside the finite period of time. In one example, the overlap of stimulation events may be based on the overlap requirement (as discussed at step 1604). In some examples, the first pulse train and the second pulse trains may be analyzed via a pulse train analyzer, such as pulse train analyzer 18 at FIG. 1. As an example, the pulse train analyzer may receive, as inputs, the first pulse train and the second pulse train from the pulse train setter. Additionally, the pulse train analyzer may also receive as input, the finite period for time from the finite time definition module, during which the first and the second pulse trains are analyzed.

Next, at 1612, the method 1600 includes identifying one or more adjustments for one or more of the first and the second pulse trains based on the overlap identified and the overlap requirement. For example, if no overlaps are identified at step 1610, the method may proceed to provide the first and the second pulse trains (without any modifications) to the electrodes, such as electrodes 13 at FIG. 1. However, if overlap is identified at step 1610, the method 1600 may proceed to determine the appropriate adjustments for one or more of the first and the second pulse trains based on overlap identified and the overlap requirement. In one example, the determination of adjustments for reducing/avoiding overlap, and the adjustments of the one or more pulse trains may be performed via the pulse train setter 16. The one or more adjustments may include, at 1614, a pulse shift, which includes shifting one pulse train relatively to another pulse train (e.g. 5 ms or any other suitable value between the start of the first pulse train and of the second pulse train). In some examples, pulse shift may include a shift relative to a fixed point in time (e.g. a first pulse trains starts at t=1 millisecond (ms), a second pulse train starts at t=5 ms). Example graphs illustrating various time shifts are shown and described at least at FIGS. 3, 5, 6, 13, and 15.

Additionally or alternatively, the adjustments may include, at 1616, a temporal arrangement adaptation. This includes adjusting the first temporal arrangement and/or the second temporal arrangement within a predetermined tolerance band. In one example, the temporal arrangement for a pulse train may be indicated by frequency. Accordingly, in some examples, a predetermined frequency tolerance band may be chosen between more or less than 15% of a first frequency defining the first temporal arrangement of stimulation events and/or a second frequency defining the second temporal arrangement of stimulation events. In some other example, the predetermined frequency tolerance may be more or less than 10% of the first frequency and/or the second frequency. By choosing the tolerance band within such a range it is ensured that still similar or even the same effects of the intended neurostimulation may be achieved. Example graphs illustrating various frequency adjustments are shown and described at least at FIGS. 3, 5, 6, 13, and 15.

Furthermore, additionally or alternatively, the adjustments may include, at 1618, a pulse shape modification, which includes modifying at least partially the shape and/or phase duration of the stimulation events of the first pulse train and/or the second pulse train and/or the shape and/or phase duration of at least one phase of a stimulation event being part of the stimulation events of the first pulse train and/or the second pulse train.

Upon identifying the adjustments that may need to be made, the method 1600 proceeds to 1620. At 1620, the method 1600 includes modifying one or more of the first pulse train and the second pulse train based on the adjustments. As discussed above, the pulse train setter 16 may adjust one or more of the first and the second pulse trains based on the overlap requirement.

Next, at 1622, the method 1600 includes delivering the modified pulse trains to the electrodes, such as electrodes 13 at FIG. 1.

The technical advantages of the neurostimulation method and systems described herein include significant reduction of adverse side effects occurring from full overlap of stimulation events between multiple pulse trains, particularly, in multi-channel and /or variable neurostimulation. Another technical effect is improved efficiency in delivering neurostimulation and reduced complexity in handling unwanted overlapping of neurostimulation events by defining a finite time period for overlap evaluation. For example, by defining the finite time period, the pulse trains generated may be quickly evaluated and necessary adjustments may be performed in a more efficient manner to reduce overlap.

Note that the example control and estimation routines included herein can be used with various system configurations. The control methods and routines disclosed herein may be stored as executable instructions in non-transitory memory and may be carried out by a system 10 as described above, either by the whole system or any other system hardware or modules of the system. The specific routines described herein may represent one or more of any number of processing strategies such as event-driven, interruptdriven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of a computer readable storage medium in the system 10, its controller 12 or any of its modules, where the described actions are carried out by executing the instructions in the system 10 including the various hardware components.

REFERENCES 10 system
11 neurostimulator
12 controller
13 electrodes
14 finite time definition module
15 battery/power source
16 pulse train setter
17 overlap requirement input
18 pulse train analyzer
PT1 pulse train
PT2 pulse train
PT3 pulse train
W1 waveform
W2 waveform
W3 waveform

The invention claimed is:

1. A method for providing neurostimulation comprising:
defining a finite period of time;
providing at least a first pulse train, the first pulse train being provided on a first channel, the first pulse train comprising a first temporal arrangement of stimulation events;
providing at least a second pulse train, the second pulse train being provided on a second channel, the second pulse train comprising a second temporal arrangement of stimulation events;
analyzing the first pulse train and the second pulse train for detecting at least one potential overlap of the stimulation events of the first pulse train and the second pulse train occurring within the finite period of time;
responsive to a detected overlap within the finite period of time, adjusting one or more of the first pulse train and the second pulse train by one or more of the following to reduce at least partially the detected overlap of stimulation events occurring within the finite period of time:
a. shifting the first pulse train and the second pulse train relatively to each other;
b. adapting one or more of the first temporal arrangement and the second temporal arrangement of stimulation events within a predetermined tolerance band; and
c. modifying at least partially one or more of a shape and a phase duration of the stimulation events of one or more of the first pulse train and the second pulse train.

2. The method of claim 1, wherein the finite period of time is no longer than 10 seconds.

3. The method of claim 1, wherein the one or more of the first pulse train and the second pulse train are adjusted to completely avoid the overlap of stimulation events.

4. The method of claim 1, wherein the one or more of the first pulse train and the second pulse train are adjusted to partially reduce the overlap of stimulation events.

5. The method of claim 1, wherein the tolerance band is between more or less than 15% of a first frequency defining the first temporal arrangement of stimulation events and a second frequency defining the second temporal arrangement of stimulation events.

6. The method of claim 1, wherein the first pulse train is a first a periodic waveform and the second pulse train is a second aperiodic waveform; and wherein the tolerance band of a first and/or second instantaneous frequency of the first and/or second aperiodic waveforms is between more or less than 15% of an average frequency of the first and/or second aperiodic waveform.

7. The method of claim 1, further comprising providing one or more additional pulse trains.

8. The method of claim 1, wherein the first pulse train is a first aperiodic waveform and the second pulse train is a second aperiodic waveform; and wherein the tolerance band of a first and/or second instantaneous frequency of the first and/or second aperiodic waveforms is between more or less than 10% of an average frequency of the first and/or second aperiodic waveform.

9. The method of claim 1, further comprising performing a second analysis on adjusted first pulse train and adjusted second pulse train for detecting at least another potential overlap of stimulation events of the adjusted first pulse train and the adjusted second pulse train.

10. A system for neurostimulation, comprising: at least one pulse train setter configured for providing at least a first pulse train, the first pulse train comprising a first temporal arrangement of stimulation events; and at least a second pulse train, the second pulse train comprising a second temporal arrangement of stimulation events;
a plurality of electrodes for delivering neurostimulation to a patient;
a controller configured with instructions in non-transitory memory that when executed cause the controller to:
define a finite period of time and analyze the first pulse train and the second pulse train for at least one potential overlap of stimulation events of the first pulse train and the second pulse train occurring within the finite period of time; and wherein the pulse train setter is further configured with instructions in non-transitory memory that cause pulse train setter to:
responsive to a detected overlap within the finite period of time, adjusting one or more of the first pulse train and the second pulse train by one or more of the following to at least partially reduce the detected overlap of stimulation events between the first pulse train and the second pulse train occurring within the finite period of time:
a. shifting the first pulse train and the second pulse train relatively to each other;
b. adapting the first temporal arrangement and/or the second temporal arrangement within a predetermined tolerance band; and
c. modifying at least partially one or more of a shape and a phase duration of one or more of the stimulation events of the first pulse train and the second pulse train.

11. The system of claim 10, wherein the finite period of time is no longer than 10 seconds.

12. The system of 10, wherein the one or more of the first pulse train and the second pulse train are adjusted to completely avoid overlap between first stimulation events of the first pulse train and second stimulation events of the second pulse train.

13. The system of claim 10, wherein the one or more of the first pulse train and the second pulse train are adjusted to partially reduce overlap between first stimulation events of the first pulse train and second stimulation events of the second pulse train.

14. The system of claim 10, wherein the tolerance band is chosen between more or less than 15% of a first frequency of first stimulation events of the first pulse train and a second frequency of second stimulation events of the second pulse train.

15. The system of claim 10, wherein the first pulse train is a first a periodic waveform and the second pulse train is a second aperiodic waveform; and wherein the tolerance band of a first and/or second instantaneous frequency of the first and/or second aperiodic waveforms is between more or less than 15% of an average frequency of the first and/or second aperiodic waveform.

16. The system of claim 10, wherein more than two pulse trains are provided.

17. The system of claim 10, wherein the tolerance band is chosen between more or less than 10% of a first frequency of first stimulation events of the first pulse train and a second frequency of second stimulation events of the second pulse train.

18. The system of claim 10, wherein analyzing the first pulse train and the second pulse train for at least one potential overlap is based on an overlap requirement.

19. The system of claim 10, wherein an overlap requirement is based on user input.

\* \* \* \* \*